(12) United States Patent
Burli et al.

(10) Patent No.: US 7,498,349 B2
(45) Date of Patent: Mar. 3, 2009

(54) BIARYL COMPOUNDS HAVING ANTI-INFECTIVE ACTIVITY

(75) Inventors: Roland W. Burli, Pasadena, CA (US); Eldon E. Baird, Lexington, SC (US); Jacob A. Kaizerman, Redwood City, CA (US); Dustin L. McMinn, South San Francisco, CA (US)

(73) Assignee: Genesoft Pharmaceuticals, Inc., South San Francisco, CA (US)

( * ) Notice: Subject to any disclaimer, the term of this patent is extended or adjusted under 35 U.S.C. 154(b) by 344 days.

(21) Appl. No.: 10/523,422

(22) PCT Filed: Aug. 1, 2003

(86) PCT No.: PCT/US03/24294

§ 371 (c)(1), (2), (4) Date: Oct. 6, 2005

(87) PCT Pub. No.: WO2004/012736

PCT Pub. Date: Feb. 12, 2004

(65) Prior Publication Data

US 2006/0128747 A1    Jun. 15, 2006

Related U.S. Application Data

(60) Provisional application No. 60/400,671, filed on Aug. 2, 2002.

(51) Int. Cl.
*A61K 31/343* (2006.01)
*A61K 31/427* (2006.01)
*A61K 31/4355* (2006.01)
*A61K 31/444* (2006.01)
*A61K 31/443* (2006.01)
*C07D 471/04* (2006.01)
*C07D 401/12* (2006.01)
*C07D 405/14* (2006.01)
*C07D 409/14* (2006.01)
*C07D 275/03* (2006.01)
*C07D 307/81* (2006.01)

(52) U.S. Cl. .............. 514/333; 514/302; 514/339; 514/337; 514/338; 514/372; 514/469; 546/115; 546/256; 546/277.4; 546/281.1; 546/284.1; 548/206; 548/214; 549/469

(58) Field of Classification Search .............. 514/302, 514/333, 339, 337, 338, 372, 469; 546/115, 546/256, 277.4, 281.1, 284.1; 548/206, 214; 549/469
See application file for complete search history.

(56) References Cited

U.S. PATENT DOCUMENTS

| | | | |
|---|---|---|---|
| 3,622,574 A | 11/1971 | Wright et al. | |
| 4,738,980 A | 4/1988 | Arcamone et al. | |
| 4,766,142 A | 8/1988 | Arcamone et al. | |
| 4,800,211 A | 1/1989 | Tischler et al. | |
| 4,912,199 A | 3/1990 | Lown et al. | |
| 5,017,599 A | 5/1991 | Lazzari et al. | |
| 5,049,579 A | 9/1991 | Lazzari et al. | |
| 5,310,752 A | 5/1994 | Lazzari et al. | |
| 5,350,748 A | 9/1994 | Boschelli et al. | |
| 5,395,849 A | 3/1995 | Wittman et al. | |
| 5,472,976 A | 12/1995 | Animati et al. | |
| 5,502,068 A | 3/1996 | Lown et al. | |
| 5,545,640 A | 8/1996 | Beaulieu et al. | |
| 5,616,606 A | 4/1997 | Lown et al. | |
| 5,670,534 A | 9/1997 | Animati et al. | |
| 5,698,674 A | 12/1997 | Bruice et al. | |
| 5,753,629 A | 5/1998 | Beria et al. | |
| 5,801,155 A | 9/1998 | Kutyavin et al. | |
| 5,808,087 A | 9/1998 | Matsunaga et al. | |
| 5,821,258 A | 10/1998 | Matsunaga | |
| 5,844,110 A | 12/1998 | Gold | |
| 5,852,011 A | 12/1998 | Matsunaga et al. | |
| 5,998,140 A | 12/1999 | Dervan et al. | |
| 6,090,947 A | 7/2000 | Dervan et al. | |
| 6,143,901 A | 11/2000 | Dervan | |
| 6,153,642 A | 11/2000 | Cozzi et al. | |
| 6,172,104 B1 | 1/2001 | Tidwell et al. | |
| 6,458,768 B1 | 10/2002 | Cozzi et al. | |
| 6,555,693 B2 | 4/2003 | Ge et al. | |
| 6,566,393 B1 | 5/2003 | Lee et al. | |
| 6,586,561 B1 | 7/2003 | Litt et al. | |
| 6,716,866 B2 | 4/2004 | McMinn et al. | |

(Continued)

FOREIGN PATENT DOCUMENTS

DE    199 20 936 A1    11/2000

(Continued)

OTHER PUBLICATIONS

Arcamone, F. et al., "Synthesis, DNA binding and antiviral activity of distamycin analogues containing different heterocyclic moieties." *Anti-Cancer Drug Design*, 1:235-244 (1986).

(Continued)

*Primary Examiner*—Kamal A Saeed
*Assistant Examiner*—Jason Nolan
(74) *Attorney, Agent, or Firm*—Townsend and Townsend and Crew LLP

(57) ABSTRACT

Aromatic compounds exemplified by exhibit antimicrobial activity.

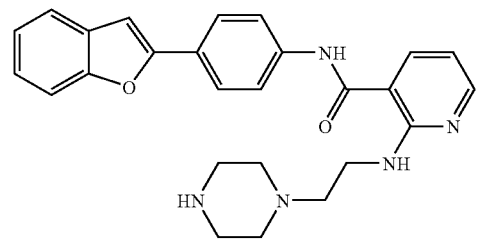

13 Claims, 7 Drawing Sheets

U.S. PATENT DOCUMENTS

| | | | |
|---|---|---|---|
| 6,777,425 | B2 | 8/2004 | Bürli et al. |
| 6,825,228 | B2 | 11/2004 | Bürli et al. |
| 2003/0199516 | A1 | 10/2003 | Moser et al. |
| 2003/0211508 | A1 | 11/2003 | Ge et al. |
| 2003/0236198 | A1 | 12/2003 | Bürli et al. |
| 2005/0004042 | A1 | 1/2005 | Hu et al. |

FOREIGN PATENT DOCUMENTS

| | | |
|---|---|---|
| EP | 1 344 525 A1 | 9/2003 |
| GB | 2 310 207 A | 2/1996 |
| JP | 08-027146 A | 10/1996 |
| JP | 08-269008 A | 10/1996 |
| JP | 11-171886 A | 6/1999 |
| JP | 11-189594 A | 7/1999 |
| WO | WO 92/13838 A1 | 8/1992 |
| WO | WO 93/13739 A2 | 7/1993 |
| WO | WO 94/20463 A1 | 9/1994 |
| WO | WO 95/24419 A1 | 9/1995 |
| WO | WO 96/26950 A1 | 9/1996 |
| WO | WO 97/03957 A1 | 2/1997 |
| WO | WO 97/25351 A2 | 7/1997 |
| WO | WO 97/28123 A1 | 8/1997 |
| WO | WO 98/21202 A1 | 5/1998 |
| WO | WO 98/35702 A1 | 8/1998 |
| WO | WO 98/37066 A1 | 8/1998 |
| WO | WO 98/37067 A1 | 8/1998 |
| WO | WO 98/37087 A1 | 8/1998 |
| WO | WO 98/43663 A1 | 10/1998 |
| WO | WO 98/45284 A1 | 10/1998 |
| WO | WO 98/49142 A1 | 11/1998 |
| WO | WO 98/50582 A1 | 11/1998 |
| WO | WO 98/52614 A2 | 11/1998 |
| WO | WO 99/00364 A1 | 1/1999 |
| WO | WO 99/25686 A1 | 5/1999 |
| WO | WO 99/27939 A1 | 6/1999 |
| WO | WO 99/41367 A1 | 8/1999 |
| WO | WO 99/50265 A1 | 10/1999 |
| WO | WO 99/50266 A1 | 10/1999 |
| WO | WO 99/62890 A1 | 12/1999 |
| WO | WO 99/64413 A1 | 12/1999 |
| WO | WO 00/06541 A1 | 2/2000 |
| WO | WO 00/06542 A1 | 2/2000 |
| WO | WO 00/15209 A2 | 3/2000 |
| WO | WO 00/15773 A2 | 3/2000 |
| WO | WO 00/40605 A2 | 7/2000 |
| WO | WO 00/69432 A1 | 11/2000 |
| WO | WO 01/10439 A1 | 2/2001 |
| WO | WO 01/19792 A1 | 3/2001 |
| WO | WO 01/21615 A1 | 3/2001 |
| WO | WO 01/74898 A2 | 10/2001 |
| WO | WO 01/96313 A1 | 12/2001 |
| WO | WO 02/00650 A2 | 1/2002 |
| WO | WO 02/51397 A1 | 4/2002 |
| WO | WO 02/088119 A1 | 11/2002 |
| WO | WO 02/101073 A2 | 12/2002 |
| WO | WO 2004/012736 A1 | 2/2004 |

OTHER PUBLICATIONS

Bailly, C. and J.B. Chaires, "Sequence-specific DNA minor groove binders, Design and synthesis of netropsin and distamycin analogues." *Bioconj. Chem.*, 9(5):513-538 (1998).

Baird, E.E. and P.B. Dervan, "Solid phase synthesis of polyamides containing imidazole and pyrrole amino acids." *J. Am. Chem. Soc.*, 118:6141-46 (1996).

Baraldi et al., "Synthesis of 3-Substituted-7-alkoxy-5H-pyrazolo [4,3-d],2,3-triazin-4(3H)-ones" *Synthesis*, pp. 1437-1440, (1994), XP002208604.

Baraldi, P.G. et al., "Synthesis and antitumor activity of new benzoheterocyclic derivatives of distamycin A." *J. Med. Chem.*, 43:2675-2684 (2000).

Berge, S.M., et al, "Pharmaceutical Salts", *J. Pharm. Sci.*, 66:1-19 (1977).

Bilder G. et al., "Restenosis following angioplasty in the swine coronary artery is inhibited by an orally active PDGF-receptor tyrosine kinase inhibitor, RPR101511A." *Circulation*, 99(25):3292-99 (1999).

Boger, D.L. et al., "A simple, high-resolution method for establishing DNA binding affinity and sequence selectivity." *J. Am. Chem. Soc.*, 123:5878-91 (2001).

Boger, D.L. et al., "Total synthesis of distamycin A and 2640 analogues: A solution-phase combinatorial approach to the discovery of new bioactive DNA binding agents and development of a rapid high-throughput screen for determining relative DNA binding affinity or DNA binding sequence selectivity." *J. Am. Chem. Soc.*, 122:6382-94 (2000).

Bremer, R.E. et al., "Recognition of the DNA minor groove by pyrrole-imidazole polyamides: comparison of desmethyl-and n-methylpyroole." *Bioorg. Med. Chem.*, 8:1947-55 (2000).

Bruice, Thomas C. et al., "Rational design of substituted tripyrrole peptides that complex with DNA by both selective minor-groove binding and electrostatic interaction with the phosphate backbone." *Proc. Natl. Acad. Sci. USA*, 89:1700-04 (1992).

Chiarino, D. et al., "Synthesis of new isoxazole aminoalcohols." *J. Heterocyclic Chem.*, 25(1):337-342 (1988).

Choudhury, G.G. et al., "Involvement of PKC-alpha in PDGF-mediated mitogenic signaling in human mesangial cells." *Am. J. Physiol.*, 265(5 Pt 2):F634-42 (1993).

Corallini, A. et al. "Characterization of the effects of two polysulfonated distamycin A derivatives, PNU145156E and PNU153429, on HIV type 1 Tat protein." *AIDS Res. Hum. Retroviruses*, 4(17):1561-71 (1998).

Dyatkina, N.B. et al., "Minor groove DNA binders as antimicrobial agents. 1. Pyrrole tetraamides are potent antibacterials against vancomycin resistant *Enterococci* [corrected] and methicillin resistant *Staphylococcus aureus*." *J. Med. Chem.*; 45(4):805-17 (2002).

Ellervik, U. et al., "Hydroxybenzamide/pyrrole pair distinguishes T·A from A·T base pairs in the minor groove of DNA" *J. Am. Chem. Soc.* 122(39):9354-60 (2000).

El-Naggar, A.M. et al., "Synthesis of some 2-thenoyl-, 5-bromo-2-thenoyl- and 5-nitro-2-thenoylamino acid derivatives and their antimicrobial activity." *J. Indian Chem. Soc.*, LIX:783-786 (1982).

Fenwick et al., "Solid-phase synthesis of cyclic alkoxyketones, inhibitors of the cysteine protease cathepsin K." *Bioorg. Med. Chem. Lett.*, 11:195-98 (2001).

Floreancig, P.E. et al., "Recognition of the minor groove of DNA by hairpin polyamides containing alpha-substituted-beta-amino acids." *J. Am. Chem. Soc.*, 122:6342-50 (2000).

Goodsell D. and R.E. Dickerson, "Isohelical analysis of DNA groove-binding drugs." *J. Med. Chem.*, 29(5):727-33 (1986).

Gougerot-Pocidalo, M.A. et al. "Mechanisms by which oxidative injury inhibits the proliferative response of human lymphocytes to PHA. Effect of the thiol compound 2-mercaptoethanol." *Immunology*; 64(2):281-8 (1988).

Gupta et al., "Hybrid molecules containing propargylic sulfones and DNA minor groove-binding lexitropsins: synthesis, sequence specificity of reaction with DNA and biological evaluation." *Gene*, 149:81-90 (1994).

Handler, J.A. et al., "Mitogenic signaling by epidermal growth factor (EGF), but not platetet-derived growth factor, requires arachidonic acid metabolism in BALB/c 3T3 cells. Modulation of EGF-dependent c-myc expression by prostaglandins." *J. Biol. Chem.*, 265(7):3669-73 (1990).

Heldin C.H. and B. Westermark, "Mechanism of action and in vivo role of platelet-derived growth factor." *Physiol. Rev.*; 79(4):1283-316 (1999).

Herman, D.M. et al., "Cycle Polyamide Motif for Recognition of the Minor Groove of DNA." *J. Am. Chem. Soc.*, 121(6):1121-29 (1999).

Kelly, J.J. et al., "Binding site size limit of the 2:1 pyrrole-imidazole polyamide-DNA motif." *Proc. Natl. Acad. Sci. USA*, 93:6981-85 (1996).

Khalaf, A.I. et al., "The synthesis of some head to head linked DNA minor groove binders." *Tetrahedron*, 56:5225-39 (2000).

Kopka, M.L. et al., "Defining GC-specificity in the minor groove: sibe-by-side binding of the di-imidazole lexitropsin to C-A-T-G-G-CC-A-T-G." *Structure*, 5(8):1033-46 (1997).

Machon, Z. and S. Ryng, "Synthesis and biological properties of 5-benzoylamino-3-methyl-4-isoxazolocarboxylic acid derivatives." *Arch. Immunol. Ther. Exp. (Warsz).*, 29(6):813-21 (1981).

Matsuba, Y. et al., "A novel synthetic DNA minor groove binder, MS-247: antitumor activity and cytotoxic mechanism." *Cancer Chemo. Pharm.*, 46:1-9 (2000).

Matsumoto, T. et al., "Synthesis of sulfonamido oligo-*N*-methylpyrrole-carboxamide derivatives and their photochemical DNA cleaving activities." *Heterocycles*, 33(1):135-138 (1992).

Matusomoto, T. et al. "Synthesis of halogenated oligo-*N*-methylpyrrole-carboxamide derivatives and their photochemical DNA cleaving activities." *Heterocycles*, 34(9):1697-1702 (1992).

Mrksich, M. et al., "Hairpin peptide motif, a new class of oligopeptides for sequence-specific recognition in the minor groove of double-helical DNA." *J. Am. Chem. Soc.*116:7983-88 (1994).

Neidle, S., "DNA minor-groove recognition by small molecules." *Nat. Prod. Rep.*, 18:291-309 (2001).

Nguyen, J.T. et al. "Exploiting the basis of proline recognition by SH3 and WW domains: design of N-substituted inhibitors." *Science*, 282(5396):2088-92 (1998).

Nielsen, P.E. "Sequence-Selective DNA Recognition by Synthetic Ligands." *Bioconjug. Chem.*, 2(1):1-12 (1991).

Pae, A.N. et al., "Synthesis and in vitro activity of new oxazolidinone antibacterial agents having substituted isoxazoles", *Bioorg. Med. Chem. Lett.*, 9:2679-84 (1999).

Plescia, S. et al., "3α-hydroxysteroid dehydrogenase inhibitory activity of some N(3)-(1-R-4-carboxypyrazol-5-yl)-1,2,3-benzotriazin-4(3H)-one and quinazoline-4(3H)-one acids." *Il Farmaco*, 49(7,8):505-07 (1994).

Plouvier, B. et al., "DNA-sequence specific recognition by a thiazole analogue of netropsin: a comparative footprinting study." *Nucl. Acids Res.*, 19(21):5821-5829 (1991).

Rao, K.E. et al., "Interaction of synthetic analogues of distamycin and netropsin with nucleic acids. Does curvature of ligand play a role in distamycin-DNA interactions?" *Biochemistry*, 27(8):3018-24 (1988).

Rao, K.E. et al., "Molecular recognition between oligopeptides and nucleic acids: DNA sequence specificity and binding properties of thiazole-lexitropsins incorporating the concepts of base site acceptance and avoidance." *Anti-Cancer Drug Design*, 5:3-20 (1990).

Renkema, G.H. and K. Saksela, "Interactions of HIV-1 NEF with cellular signal transducing proteins," *Frontiers in Bioscience*, 5:d268-83 (2000).

Sakai, Y. et al.,"Synthesis of halogenated thiazole derivatives of oligo-*N*-methylpyrrolecarboxamide and their photochemical DNA cleaving activities." *Heterocycles*, 36(3):565-73 (1993).

Sen et al., "Synthesis of Compounds Related to Reserpine Skeleton." *J. Indian Chem. Soc.*, 46(3):209-15, also in *Chemical Abstracts* 71(1):318 (1969).

Sharma et al., "Design and Synthesis of Novel Thiazole-Containing Cross-Linked Polyamides Related to the Antiviral Antibiotic Distamycin." *J. Org. Chem*, p. est: 5.3 (1999).

Tanis, Steven P. and David B. Head, "Furans in synthesis. The preparation of (.+−.)-lactaral", *Tetrahedron Lett.*, 23:(52) pp. 5509-5512 (1982).

Taylor, J.S. et al., "DNA affinity cleaving : Sequence specific cleavage of DNA by Distamycin-EDTA—Fe(II) and EDTA-distamycin Fe(II)." *Tetrahedron*, 40(3):457-65 (1984).

Trauger, J.W. et al., "Recognition of DNA by designed ligands at subnanomolar concentrations." *Nature*, 382:559-61 (1996).

Vaquero et al., "Small ligands that neither bind to nor alter the structures of d(GA.TC)n sequences in DNA." *FEBS Letters*, 420:156-60 (1997).

Wade W.S. et al., "Binding affinities of synthetic peptides, pyridine-2-carboxamidonetropsin and 1-methylimidazole-2-carboxamidonetropsin, that form 2:1 complexes in the minor groove of double-helical DNA." *Biochemistry*, 32(42):11385-89 (1993).

Wade, W.S. et al., "Design of peptides that bind in the minor groove of DNA at 5'-(A,T)G(A,T)C(A,T)-3' sequences by a dimeric side-by-side motif." *J. Am. Chem. Soc.*, 114(23):8783-94 (1992).

Wade, W.S., "Sequence specific complexation of B DNA at sites containing G,C base pairs." Ph.D. Thesis, California Institute of Technology, Pasadena, CA (1989).

White, S. et al., "Recognition of the four Watson-Crick base pairs in the DNA minor groove by synthetic ligands." *Nature*, 391:468-71 (1998).

White, S. et al., "On the pairing rules for recognition in the minor groove of DNA by pyrrole-imidazole polyamides." *Chemistry & Biology*, 4:569-578 (1997).

Xie, G. et al., "Protein kinase C-α inhibitors; structure-activity relationships in bis-indole series." *Bioorg. Med. Chem. Lett.*, 5(5):497-500 (1995).

Xie, G. et al., Synthesis and DNA cleaving properties of hybrid molecules containing propargylic sulfones and minor groove binding lexitropsins. *Bioorg. Med. Chem. Lett.*, 3(8):1565-70 (1993).

Xue, C.B. et al, "Synthesis and Antiplatelet Effects of An Isoxazole Series of Glycoprotein IIb/IIIa Antagonists", *Bioorg. Med. Chem. Lett.*, 8:3499-3504 (1998).

Yamori, T. et al., "Potent antitumor activity of MS-247, a novel DNA minor groove binder evaluated by an in vitro and in vivo human cancer cell line panel." *Cancer Res.*, 59(16):4042-49 (1999).

Zakrzewska, K. et al., "Drug recognition of DNA. Proposal for GC minor groove specific ligands: vinylexins." *J. Biomol. Struct. Dyn.*, 6(2):1043-1058 (1989).

Zakrzewska, K. et al., "Theoretical study of the sequence selectivity of isolexins, isohelical DNA groove binding ligands. Proposal for the GC minor groove specific compounds." *J. Biomol. Struct. Dyn.*, 5(5):1043-1058 (1988).

BIARYL COMPOUNDS HAVING ANTI-INFECTIVE ACTIVITY

CROSS-REFERENCES TO RELATED APPLICATIONS

This application claims the benefit of provisional application Ser. No. 60/400,671, filed Aug. 2, 2002, the entire contents of which are incorporated herein by reference.

STATEMENT AS TO RIGHTS TO INVENTIONS MADE UNDER FEDERALLY SPONSORED RESEARCH OR DEVELOPMENT

Not applicable

REFERENCE TO A "SEQUENCE LISTING," A TABLE, OR A COMPUTER PROGRAM LISTING APPENDIX SUBMITTED ON A COMPACT DISK

Not applicable

BACKGROUND OF THE INVENTION

1. Field of the Invention

This invention relates to aromatic compounds having antibacterial activity and methods for their synthesis and use.

2. Description of Related Art

The discovery of penicillin and other antimicrobials in the early and mid 20th century generated a period of optimism about the medical profession's ability to treat microbial infections. However, the evolution of drug-resistant microbe strains—with new ones being constantly discovered—has led an appreciation of the continuing need to develop new antimicrobials, preferably ones that are structurally different from extant ones or employ a different mechanism of action.

Exemplary recent disclosures of new antibacterial compounds include Ge et al., WO 01/74898 (2001); Baird et al., U.S. application Ser. No. 10/132,887, filed Apr. 24, 2002; Bürli et al., U.S. application Ser. No. 10/165,856, filed Jun. 6, 2002; McMinn et al., U.S. application Ser. No. 10/165,433, filed Jun. 6, 2002; Bürli et al., U.S. application Ser. No. 10/165,857, filed Jun. 6, 2002; Bürli et al., U.S. application Ser. No. 10/165,764, filed Jun. 6, 2002. Matsunaga et al., U.S. Pat. No. 5,821,258 (1998) and U.S. Pat. No. 5,852,011 (1998); and Ohemeng et al., U.S. Pat. No. 5,942,532 (1999) also disclose compounds reportedly having antimicrobial activity.

Disclosures of compounds that, even though not featured as antimicrobials, have chemical structures that may be relevant to the present invention include Matsunaga et al., U.S. Pat. No. 5,808,087 (1998); JP 11-171886 (1999); and JP 11-189594 (1999); Dykstra et al., U.S. Pat. No. 5,817,686 (1998); Neidle et al., WO 00/63180 (2000); Raspanti, U.S. Pat. No. 5,362,481 (1994); Dantzig et al., WO 97/17069 (1997); Judd, WO 94/11369 (1994); and the IDdb3 database's Drug Report for the drug Phortress (U. Nottingham).

BRIEF SUMMARY OF THE INVENTION

The present invention provides a compound (I) according to the formula

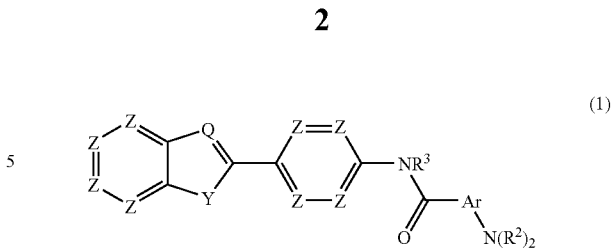

(1)

and the pharmaceutically acceptable salts thereof, wherein
each Z is independently N or $C(R^1)$, with the proviso that no more than 2 Z's in any one aromatic ring are N;
Y is O, N, or S;
Q is N or $C(R^1)$, with the proviso that Q is $C(R^1)$ when Y is N;
Ar is an aromatic or heteroaromatic 5- or 6-member ring;
each $R^1$ is independently H, halogen, OH, or a $C_1$ to $C_{12}$ alkyl or heteroalkyl moiety;
each $R^2$ is independently H or a $C_1$ to $C_{18}$ alkyl or heteroalkyl moiety or the two $R^2$'s taken together with the nitrogen atom to which they are attached form a substituted or unsubstituted heteroalkyl 5 to 7 member ring;

and
$R^3$ is H or a $C_1$ to $C_6$ alkyl moiety;
with the proviso that at least one group $R^1$, $R^2$, or $R^3$ contains an alkyl amine group or a quaternary nitrogen group.
Preferably, the alkylamino group or quaternary nitrogen group is situated in a group $R^2$.

DETAILED DESCRIPTION OF THE INVENTION

Abbreviations and Definitions

Figure 1:
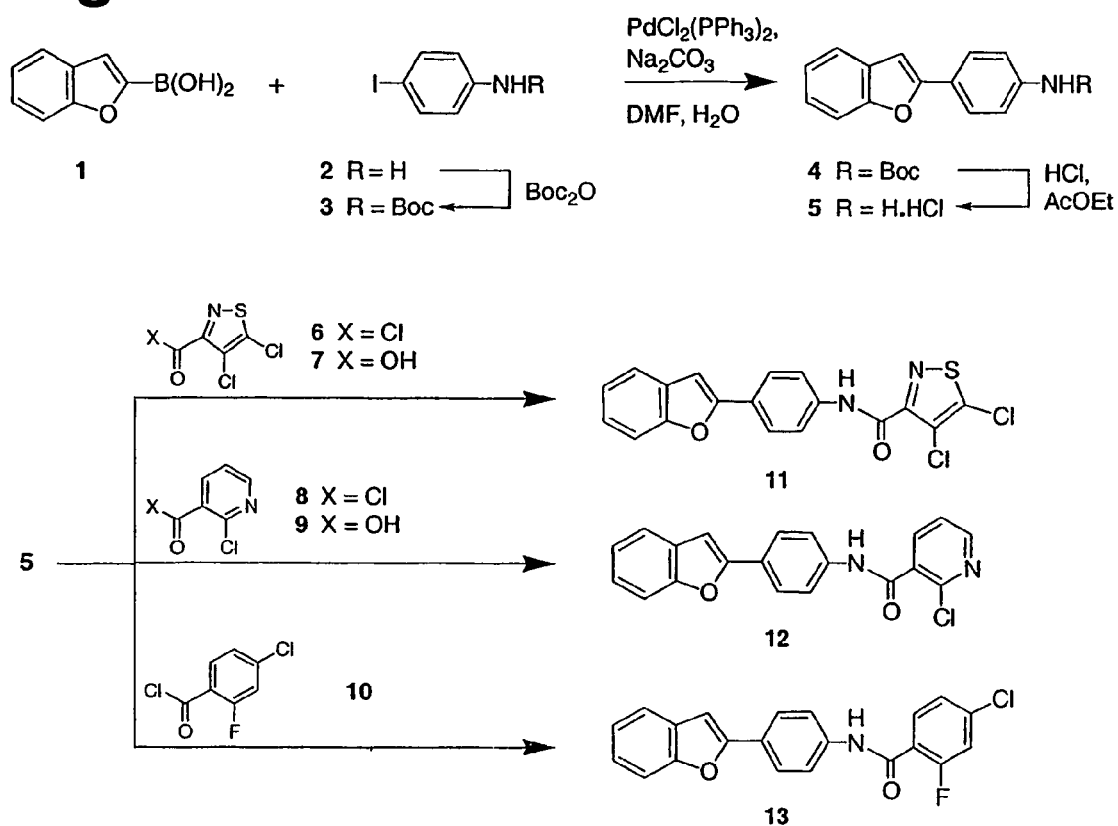
FIGS. 1 to 14 show synthetic schemes related to the preparation of compounds of this invention.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having six or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is meant to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl, heteroalkyl, aryl, and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NH—C($NH_2$)=NH, —NR'C($NH_2$)=NH, —NH—C($NH_2$)=NR', —S(O)R', —S(O)$_2$R', —S(O)$_2$NR'R", —CN and —$NO_2$ in a number ranging from zero to (2m'+1), where m' is the total number of carbon atoms in such radical. R', R" and R'" each independently refer to hydrogen, unsubstituted ($C_1$-$C_8$)alkyl and heteroalkyl, unsubstituted aryl, aryl substituted with 1-3 halogens, unsubstituted alkyl, alkoxy or thioalkoxy groups, or aryl-($C_1$-$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as halo-alkyl (e.g., —$CF_3$ and —$CH_2CF_3$) and acyl (e.g., —C(O)$CH_3$, —C(O)$CF_3$, —C(O)$CH_2OCH_3$, and the like). Preferably, the substituted alkyl and heteroalkyl groups have from 1 to 4 substituents, more preferably 1, 2 or 3 substituents. Exceptions are those perhalo alkyl groups (e.g., pentafluoroethyl and the like) which are also preferred and contemplated by the present invention.

Similarly, substituents for the aryl and heteroaryl groups are varied and are selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R'", —S(O)$_2$R', —NH—C($NH_2$)=NH, —NR'C($NH_2$)=NH, —NH—C($NH_2$)=NR', —S(O)R', —S(O)$_2$NR'R", —$N_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

Two of the substituents on adjacent atoms of the aryl or heteroaryl ring may optionally be replaced with a substituent of the formula -T-C(O)—($CH_2$)$_q$—U—, wherein T and U are independently —NH—, —O—, —$CH_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogen-carbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, ascorbic, propionic, isobutyric, maleic, malonic, lactic, malic, glutamic, benzoic, succinic, suberic, fumaric, mandelic, phthalic, benzenesulfonic, p-tolylsulfonic, citric, tartaric, methanesulfonic, lactobionic, and the like. Also included are salts of amino acids such as arginate and the like, and salts of organic acids like glucuronic or galactunoric acids and the like (see, for example, Berge, S. M., et al, "Pharmaceutical Salts", *Journal of pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (chiral centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Compounds

Preferred embodiments of compound (I) of this invention are now discussed.

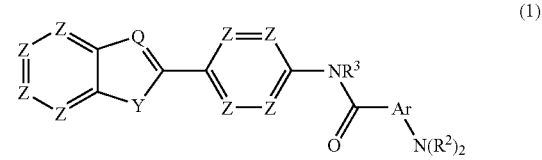

(1)

The 6,5-fused ring system in compound (I)

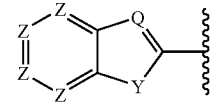

preferably is selected from the group consisting of

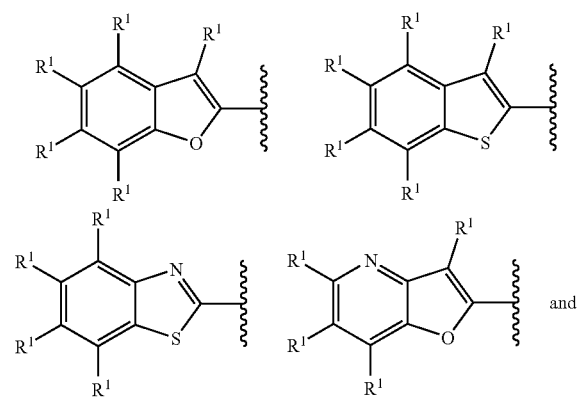

and

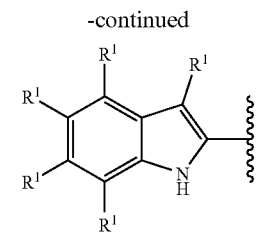

(where R¹ is as previously defined, with H and CH₃ being preferred R¹ groups); with the following 6,5-fused ring systems being particularly preferred:

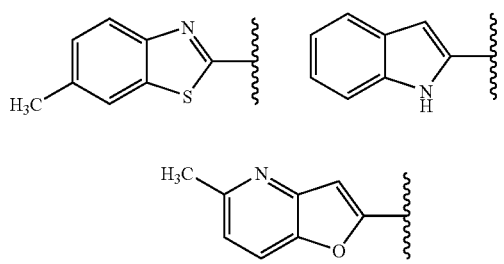

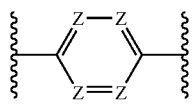

The 6-member ring

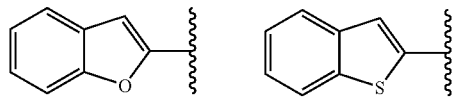

adjacent to the 6,5-fused ring system preferably is selected from the group consisting of

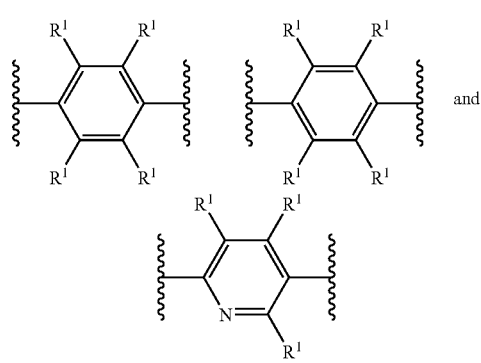

(where R¹ is as previously defined, with H and CH₃ being preferred R¹ groups); with the following 6-member rings being particularly preferred:

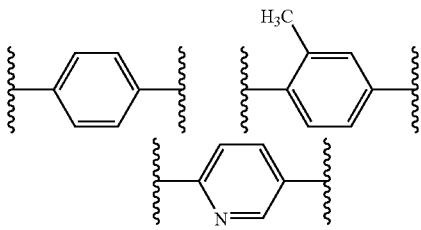

The divalent residue

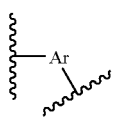

preferably is selected from the group consisting of

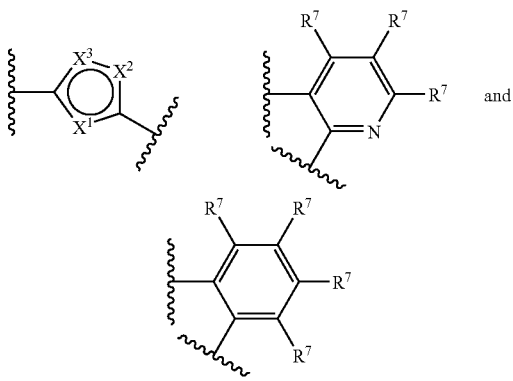

wherein one of $X^1$, $X^2$, and $X^3$ is a ring vertex selected from the group consisting of —O—, —S—, and —NR⁸—, and the other two of $X^1$, $X^2$, and $X^3$ are ring vertices selected from the group consisting of =N— and =CR⁷—; each R⁷ is independently H, F, Cl, Br, I CN, OH, NO₂, NH₂, a substituted or unsubstituted ($C_1$-$C_{12}$)alkyl group, a substituted or unsubstituted ($C_1$-$C_{12}$)alkoxy group, or a substituted or unsubstituted ($C_1$-$C_{12}$)heteroalkyl group; and R⁸ is H, a substituted or unsubstituted ($C_1$-$C_{12}$)alkyl group, or a substituted or unsubstituted ($C_1$-$C_{12}$)heteroalkyl group.

The residue

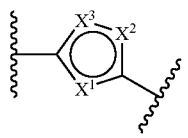

is a 5-membered ring heteroaromatic moiety, the selection of $X^1$, $X^2$, and $X^3$ determining the type of heteroaromatic ring. Exemplary heteroaromatic rings include imidazole, pyrrole, pyrazole, furan, isothiazole, oxazole, isoxazole, thiazole, furazan, 1,2,3-thiadiazole, 1,2,4-thiadiazole, 1,2,5-thiadiazole, 1,3,4-thiadiazole, 1,2,3-triazole, 1,2,4-triazole, 1,3,4-oxadiazole, 1,2,4-oxadiazole, and thiophene. The circle in the five-membered rings of formula is meant to indicate the presence of two double bonds, which, in some embodiments, can move within the ring.

Specific examples of moieties

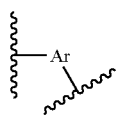

include

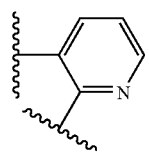 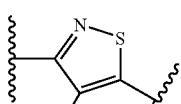 and

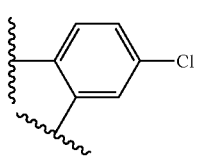

Compounds (I) have an alkyl amine group or a quaternary nitrogen group. Exemplary amine groups include

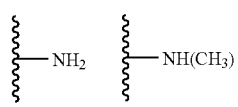

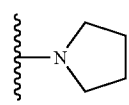 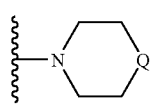

(Q = CH$_2$, O, S, NH)

and the like. Exemplary quaternary nitrogen groups include

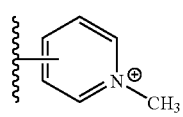 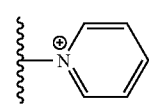 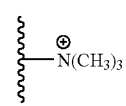

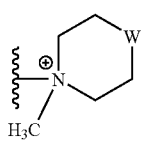

(W = CH$_2$, O, S)

In a preferred embodiment, each $R^2$ is attached to the nitrogen atom via an sp$^3$ carbon, as illustrated by the following illustrative groups $N(R^2)_2$.

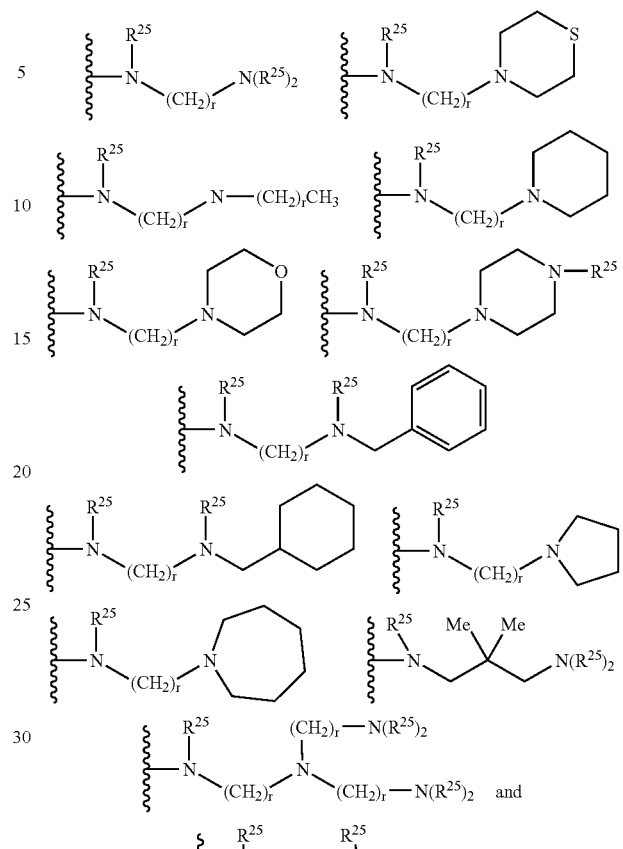

The two $R^2$'s can join together with the nitrogen atom to which they are attached to form a 5, 6, or 7 member ring, as in

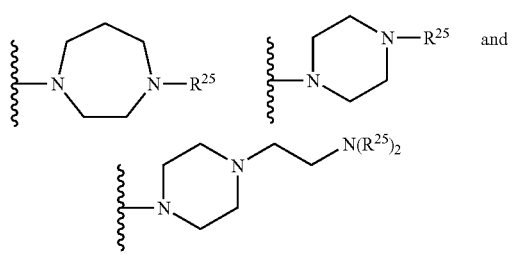

In the foregoing formulae, r is an integer ranging from 2 to 8, inclusive (preferably 2 to 6), and each $R^{25}$ is independently H, CH$_3$, CH$_2$CH$_3$, CH$_2$CH$_2$CH$_3$, or CH(CH$_3$)$_2$.

Specific preferred $N(R^2)_2$ groups include:

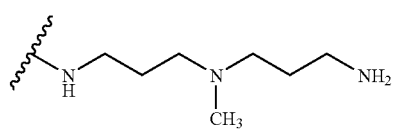

-continued
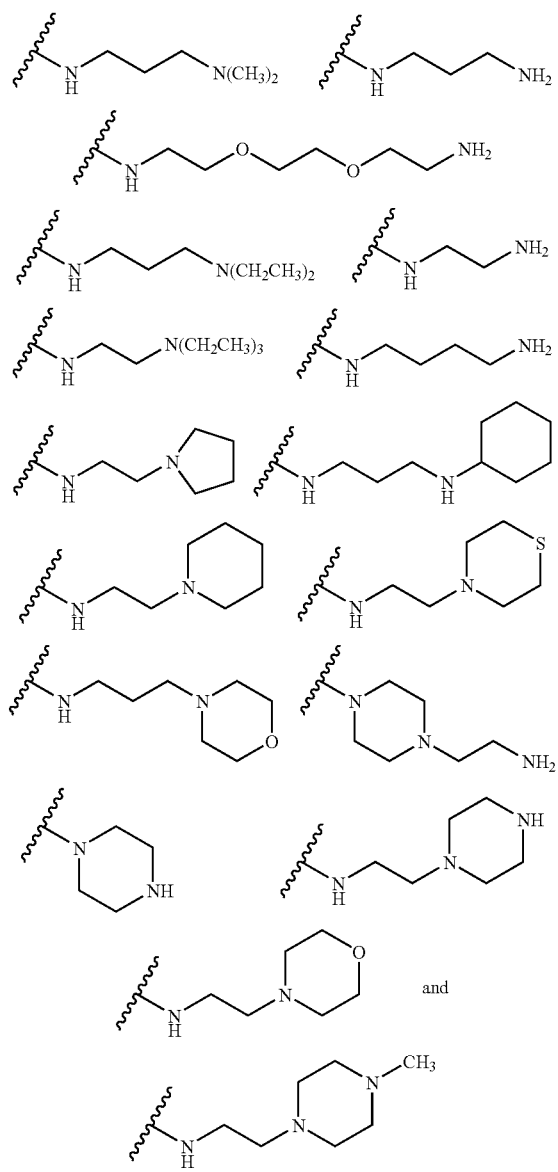
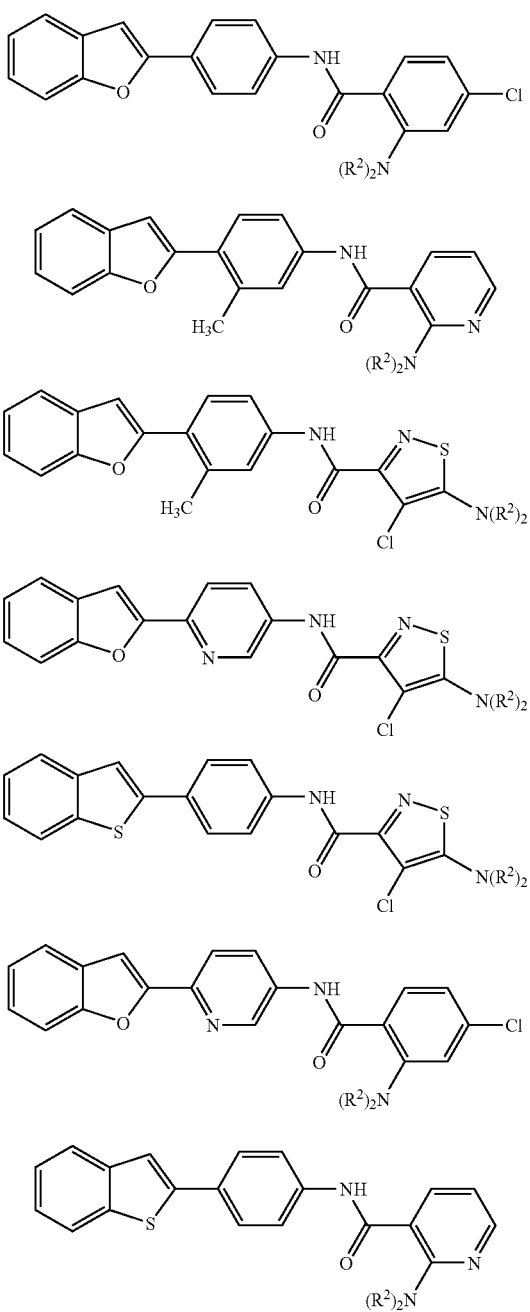
$R^3$ preferably is H, but it may be an alkyl group such as methyl, ethyl, propyl, isopropyl, butyl, t-butyl, and the like.
Preferred subgenera of compounds (I) are
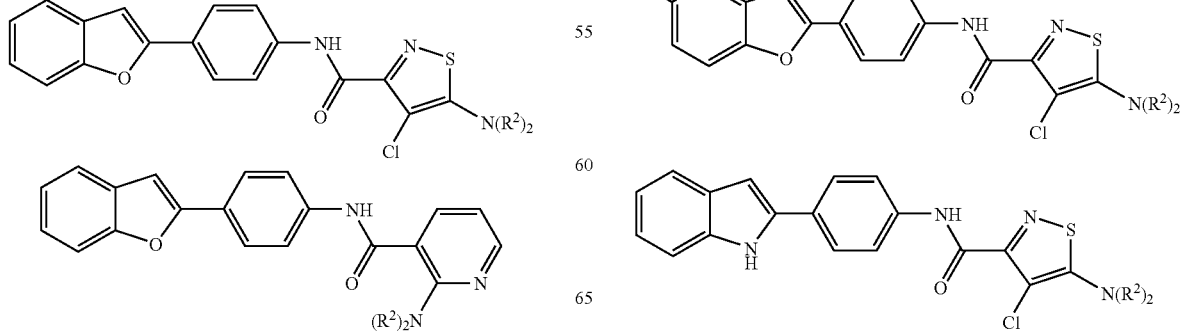

-continued

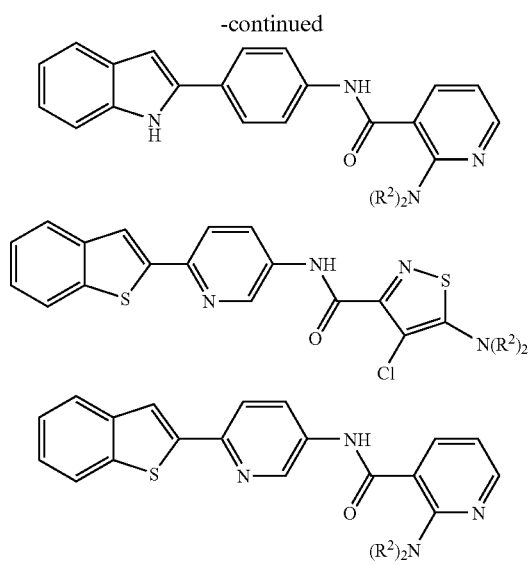

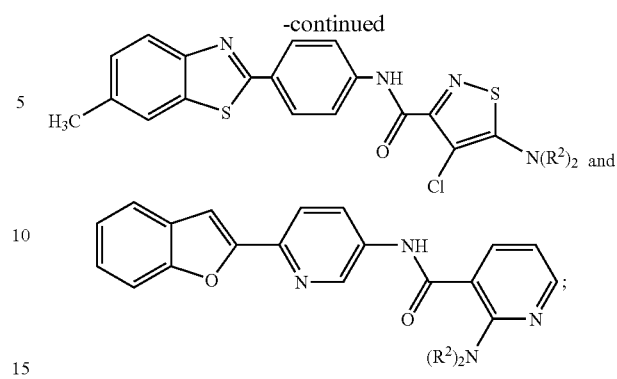

and the pharmaceutically acceptable salts thereof, wherein each $R^2$ is independently H or a $C_1$ to $C_{18}$ alkyl or heteroalkyl moiety or the two $R^2$'s taken together with the nitrogen atom to which they are attached form a substituted or unsubstituted heteroalkyl 5 to 7 member ring; at least one group $R^2$ containing an alkyl amine group.

Examples of specific compounds (I) are shown in Table A.

TABLE A

Exemplary Compounds of Formula (I)

| Ref. | ![Z-Z-Z-Z-Y-Q] | ![Z=Z-Z=Z] | ![Ar] | ![N(R²)₂] |
|---|---|---|---|---|
| A-1 | benzofuran | phenylene | 4-chloro-isothiazole | —NH—CH₂CH₂—N(piperazinyl-NH) |
| A-2 | Same | Same | Same | —NH—CH₂CH₂CH₂—NH₂ |
| A-3 | Same | Same | Same | —NH—CH₂CH₂—NH₂ |
| A-4 | Same | Same | Same | —NH—CH₂CH₂CH₂CH₂—NH₂ |
| A-5 | Same | Same | Same | —NH—CH₂CH₂CH₂—N(CH₂CH₃)₂ |
| A-6 | Same | Same | Same | —NH—CH₂CH₂—O—CH₂CH₂—O—CH₂CH₂—NH₂ |
| A-7 | Same | Same | Same | —NH—CH₂CH₂CH₂—N(CH₃)₂ |

TABLE A-continued

Exemplary Compounds of Formula (I)

| Ref. | [benzoxazole-type] | [Z=Z phenyl] | Ar | N(R²)₂ |
|---|---|---|---|---|
| A-8 | Same | Same | Same | ⁓NH-(CH₂)₃-N(CH₃)-(CH₂)₃-NH₂ |
| A-9 | Same | Same | pyridine (3,2-linked) | ⁓NH-(CH₂)₃-NH₂ |
| A-10 | Same | Same | Same | ⁓NH-CH₂CH₂-piperazine-NH |
| A-11 | Same | Same | Same | ⁓NH-(CH₂)₃-N(CH₃)₂ |
| A-12 | benzofuran | para-phenyl | pyridine (3,2-linked) | ⁓NH-(CH₂)₃-NH-cyclohexyl |
| A-13 | Same | Same | Same | ⁓NH-CH₂CH₂-piperidine |
| A-14 | Same | Same | Same | ⁓NH-CH₂CH₂-thiomorpholine |
| A-15 | Same | Same | Same | ⁓NH-CH₂CH₂-pyrrolidine |
| A-16 | Same | Same | Same | ⁓NH-(CH₂)₃-morpholine |
| A-17 | Same | Same | Same | ⁓N(piperazine)-CH₂CH₂-NH₂ |

TABLE A-continued

Exemplary Compounds of Formula (I)

| Ref. | ![Z-Z-Q-Y ring] | ![Z-Z phenyl] | ![Ar] | —N(R²)₂ |
|---|---|---|---|---|
| A-18 | Same | Same | Same | ⤳NH-(CH₂)₄-NH₂ |
| A-19 | Same | Same | Same | ⤳NH-(CH₂)₂-NH₂ |
| A-20 | Same | Same | Same | ⤳N(piperazine)NH |
| A-21 | Same | Same | Same | ⤳NH-CH₂CH₂-N(CH₂CH₃)₃ |
| A-22 | Same | Same | Same | ⤳NH-CH₂CH₂-O-CH₂CH₂-O-CH₂CH₂-NH₂ |
| A-23 | benzofuran-2-yl | 1,4-phenylene | 2,4-Cl-phenyl | ⤳NH-(CH₂)₃-N(CH₂CH₃)₂ |
| A-24 | Same | Same | Same | ⤳NH-CH₂CH₂-O-CH₂CH₂-O-CH₂CH₂-NH₂ |
| A-25 | Same | Same | Same | ⤳NH-CH₂CH₂-N(pyrrolidine) |
| A-26 | Same | Same | Same | ⤳NH-CH₂CH₂-N(piperazine)NH |
| A-27 | Same | 2-methyl-1,4-phenylene | pyridin-3-yl | ⤳NH-CH₂CH₂-N(piperidine) |
| A-28 | Same | Same | Same | ⤳NH-CH₂CH₂-N(piperazine)NH |

TABLE A-continued
Exemplary Compounds of Formula (I)
| Ref. | 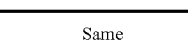 | 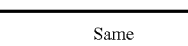 | Ar | —N(R²)₂ |
|---|---|---|---|---|
| A-29 | Same | Same | Same | 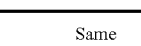 |
| A-30 | Same | Same | Same | 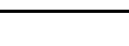 |
| A-31 | Same | Same | Same | 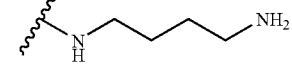 |
| A-32 | Same | Same | 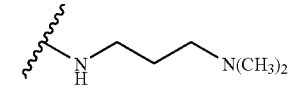 | 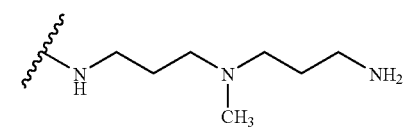 |
| A-33 | Same | Same | Same | 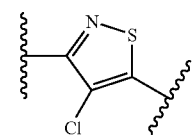 |
| A-34 | 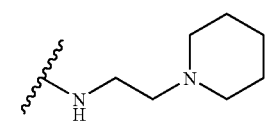 | 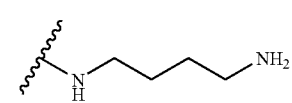 | 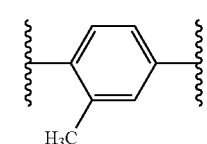 | 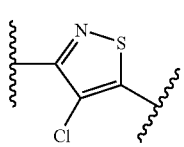 |
| A-35 | Same | 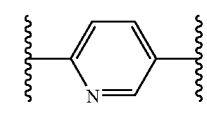 | Same | 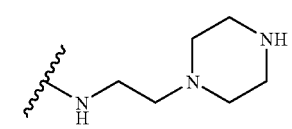 |
| A-36 | Same | Same | Same | 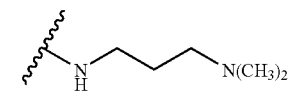 |
| A-37 | Same | Same | Same | 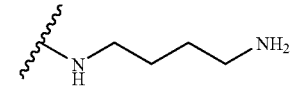 |
| A-38 | Same | Same | Same | 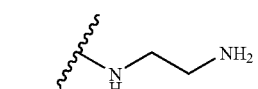 |
| A-39 | Same | Same | 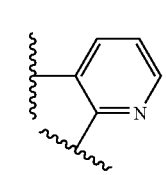 | 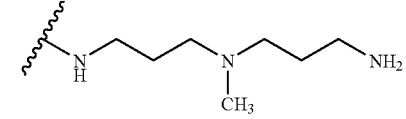 |

TABLE A-continued
Exemplary Compounds of Formula (I)
| Ref. | 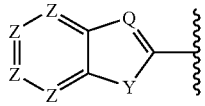 | 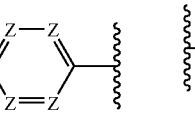 | 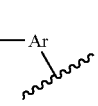 Ar | 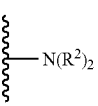 -N(R²)₂ |
|---|---|---|---|---|
| A-40 | Same | Same | Same | 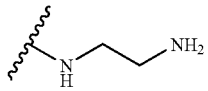 |
| A-41 | Same | Same | 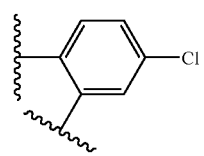 | 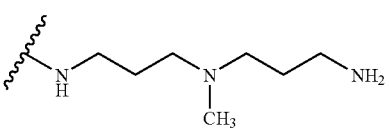 |
| A-42 | Same | Same | Same | 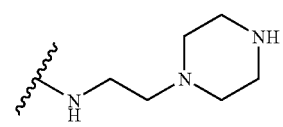 |
| A-43 | Same | Same | Same | 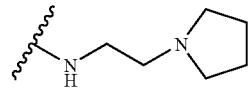 |
| A-44 | Same | Same | Same | 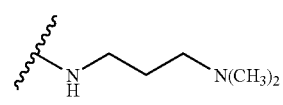 |
| A-45 | 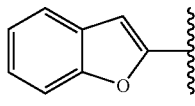 | 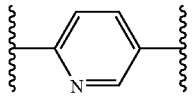 | 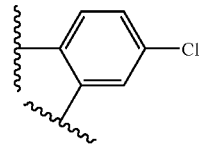 | 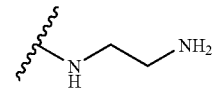 |
| A-46 | 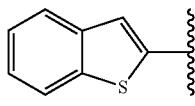 | 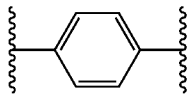 | 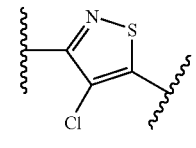 | 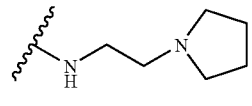 |
| A-47 | Same | Same | Same | 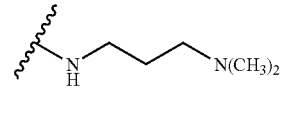 |
| A-48 | Same | Same | 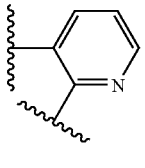 | 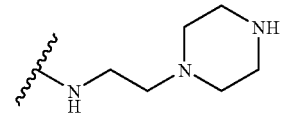 |
| A-49 | Same | Same | Same | 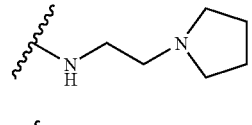 |
| A-50 | Same | Same | Same | 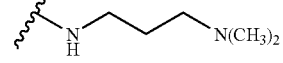 |

TABLE A-continued

Exemplary Compounds of Formula (I)

| Ref. | ![Z-Z-Q-Y structure] | ![Z-Z-Z-Z structure] | ![Ar structure] | ![N(R²)₂ structure] |
|---|---|---|---|---|
| A-51 | 6-methylbenzothiazol-2-yl | Same | 4-chloroisothiazole-3,5-diyl | —NH—CH₂CH₂CH₂—N(CH₃)—CH₂CH₂CH₂—NH₂ |
| A-52 | Same | Same | Same | —NH—CH₂CH₂—NH₂ |
| A-53 | Same | Same | Same | —NH—CH₂CH₂CH₂—NH₂ |
| A-54 | Same | Same | Same | —NH—CH₂CH₂CH₂—N(CH₃)₂ |
| A-55 | 5-methylfuro[3,2-b]pyridin-2-yl | Same | Same | Same |
| A-56 | 1H-indol-2-yl | 1,4-phenylene | 4-chloroisothiazole-3,5-diyl | —NH—CH₂CH₂—NH₂ |
| A-57 | Same | Same | Same | —NH—CH₂CH₂CH₂—N(CH₃)₂ |
| A-58 | Same | Same | Same | —NH—CH₂CH₂—(pyrrolidin-1-yl) |
| A-59 | Same | Same | Same | —NH—CH₂CH₂—(piperazin-1-yl) |
| A-60 | Same | Same | Same | —NH—CH₂CH₂—(morpholin-4-yl) |
| A-61 | Same | Same | Same | —NH—CH₂CH₂—(4-methylpiperazin-1-yl) |

TABLE A-continued

Exemplary Compounds of Formula (I)

| Ref. | ![Z-Z-Q-Y] | ![Z-Z ring] | ![Ar] | $-N(R^2)_2$ |
|---|---|---|---|---|
| A-62 | Same | Same | pyridine (3,2-linked) | -NH-CH₂CH₂-NH₂ |
| A-63 | Same | Same | Same | -NH-CH₂CH₂CH₂-N(CH₃)₂ |
| A-64 | Same | Same | Same | -NH-CH₂CH₂-piperazine-NH |
| A-65 | Same | Same | Same | -NH-CH₂CH₂-N(piperazine)-CH₃ |
| A-66 | indole (2-linked, NH) | phenyl (1,4) | pyridine (3,2-linked) | -NH-CH₂CH₂-morpholine |
| A-67 | benzothiophene (2-linked) | pyridine (2,5-linked) | 4-chloroisothiazole | -NH-CH₂CH₂CH₂-N(CH₃)₂ |
| A-68 | Same | Same | Same | -NH-(CH₂)₄-NH₂ |
| A-69 | Same | Same | Same | -NH-CH₂CH₂-piperidine |
| A-70 | Same | Same | Same | -NH-CH₂CH₂-piperazine-NH |
| A-71 | Same | Same | Same | -NH-(CH₂)₃-N(CH₃)-(CH₂)₃-NH₂ |

TABLE A-continued

Exemplary Compounds of Formula (I)

| Ref. | ![Z-Z-Q-Y structure] | ![Z-Z benzene] | ![Ar] | -N(R²)₂ |
|------|---|---|---|---|
| A-72 | Same | Same | pyridyl | -NH-CH₂CH₂-piperidinyl |
| A-73 | Same | Same | Same | -NH-CH₂CH₂-piperazinyl-NH |
| A-74 | Same | Same | Same | -NH-(CH₂)₃-N(CH₃)₂ |
| A-75 | Same | Same | Same | -NH-(CH₂)₄-NH₂ |
| A-76 | Same | Same | Same | -NH-(CH₂)₃-N(CH₃)-(CH₂)₃-NH₂ |

In the entries in Table A, where a divalent residue

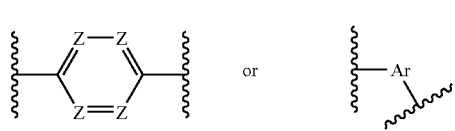

is asymmetric, it is to be inserted into formula (I) in the orientation depicted to arrive at the specific compound at issue. (This statement is not to be construed as meaning that such an asymmetric residue only can be used in compounds of this invention in the depicted orientation; in the context of a different compound, it can be used in the reversed orientation.) By way of illustration, the fully written out structure of compound A-32 is

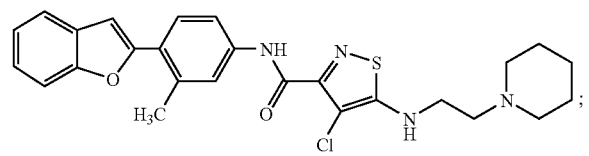

while the fully written out structure of compound A-39 is

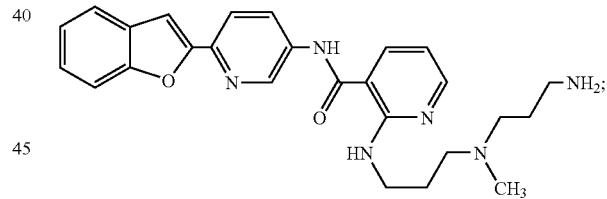

and the fully written out structure of compound A-45 is

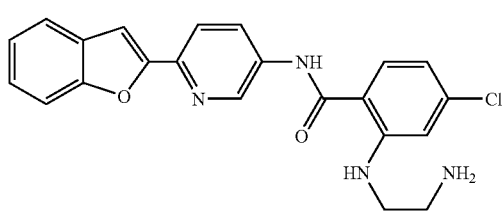

and so forth.

Compounds of this invention have been found to have anti-bacterial and/or antifungal properties and therefore may be used for combating (i.e., preventing and/or treating) infections in eukaryotic organisms. For human anti-infective applications, an effective amount of a compound of this invention is used, optionally in combination with a pharmaceutically acceptable carrier. The composition may be dry, or it may be a solution. Treatment may be reactive, for combating an existing infection, or prophylactic, for preventing infection in an organism susceptible to infection. Preferably, compounds of this invention are used to treat infections by drug-resistant strains of bacteria, for example MRSA (methicillin resistant *S. aureus*), MRSE (methicillin resistant *S. epidermidis*), PRSP (penicillin resistant *S. pneumoniae*) or VRE (vancomycin resistant *Enterococci*). By "drug-resistant" it is meant that the bacteria are resistant to treatment with conventional antibiotics.

Host organisms that can be treated include eukaryotic organisms, in particular plants and animals. The plant may be an agriculturally important crop, such as wheat, rice, corn, soybean, sorghum, and alfalfa. Animals of interest include mammals such as bovines, canines, equines, felines, ovines, porcines, and primates (including humans). Thusly, in another aspect of this invention, there is provided a method for treating a bacterial infection—particularly an infection by Gram-positive bacteria—comprising administering to a patient in need of such treatment an effective amount of compound (I). Compounds of this invention can be used in the preparation of a medicament for treating a bacterial infection in a mammal. The compounds may be administered orally, topically, parenterally (e.g., intravenously, subcutaneously, intraperitoneally, transdermally) or by inhalation.

Synthesis—General Remarks

Typically, the structures of compounds were confirmed by $^1$H-NMR and/or mass spectrometry. Where a parenthetical remark such as "$^1$H-NMR" or "mass spectrum" or "ESI-MS" follows a reference to a compound without any elaboration, it means that such spectrum was taken, was consistent with the assigned structure, and did not indicate the presence of significant impurities.

Abbreviations in common usage are employed for various technical terms, solvents, catalysts and reagents, including: HBTU for 2-(1H-benzotriazole-1-yl)-1,1,3,3-tetramethyluronium hexafluorophosphate; DIEA for diisopropylethylamine; DMF for N,N-dimethylformamide; TFA for trifluoroacetic acid; NMP for N-methylpyrrolidone; Boc for t-butyloxycarbonyl; RT for room temperature; and TLC for thin layer chromatography.

The skilled artisan will understand: (a) that an intermediate described in the context of the synthesis of a particular compound of this invention can also be used to make other compounds of this invention, *mutatis mutandis*; (b) that in certain experimental sections only the preparation of an intermediate compound is described, because its incorporation into a final compound of this invention straightforwardly follows synthetic methodology described herein; and (c) that, for some reactions that recur herein, detailed reaction and work-up conditions sometimes are not provided in each instance in the interest of brevity and that the conditions described elsewhere in this application are adaptable to the instance at hand without undue experimentation.

Synthesis—General Procedures

The following recurring general procedures are cited as "Procedure A," "Procedure B," etc. in the subsequent experimental sections.

Procedure A: Suzuki-type coupling of a boronic acid and an aryl halide. A degassed suspension of the boronic acid (1.1 equiv.), $PdCl_2(PPh_3)_2$ (0.05 equiv.), and $Na_2CO_3$ (5 equiv.) in $DMF/H_2O$ (2:1) was treated at RT under $N_2$ with a degassed ($N_2$) solution of the aryl halide (1.0 equiv.) in DMF (¼ of total volume). The mixture was heated to 80° C. for 3 hr (the reaction was followed by TLC and worked up after complete consumption of the starting material), cooled to RT, diluted with AcOEt, and washed with $H_2O$ (2×). The organic layer was dried ($MgSO_4$) and evaporated. The crude product was purified by flash chromatography to give the product as a solid.

Procedure B: Deprotection of a Boc-Protected Amine. A mixture of the Boc-protected amine (1 equiv.) in TFA was stirred at RT for 1 hr, treated with MeOH (½ of reaction volume), and left for 15 min. Evaporation of the solvent gave the deprotected amine product, used without further purification.

Procedure C: Coupling of an acid chloride to an aryl amine. A mixture of the acid chloride (1.2 equiv.) and the amine (1.0 equiv.) in DMF/DIEA (ca. 3:1) was stirred at 60° C. for 12-18 hr. The mixture was added dropwise to ice-water containing ca. 10% $K_2CO_3$ (ca. 40 fold the reaction volume). The resulting precipitate was collected by filtration and dried.

Procedure D: Nucleophilic aromatic substitution. A mixture of a dichloroisothiazole, a 2-chloronicotinamide, or a 4-chloro-2-fluorobenzamide (1 equiv.) in a solution of an amine in NMP (2:1) was stirred at 60-75° C. for 24 to 72 hr and diluted with 50% aqueous AcOH to a final volume of 15 mL (where noted below, DIEA was added to the reaction mixture). The crude product was purified by RP-HPLC (Hamilton PRP-1 column, $CH_3CN/0.5$% aq AcOH, 0% to 60% in 60 min). The purified product was characterized by $^1$H-NMR and ESI-MS).

Synthesis—Compounds

EXAMPLE A

This example describes the synthesis of compounds (I) containing a benzofuryl-phenylene moiety.

Reference is made to FIG. 1, which shows the preparation of intermediates 11 to 13. Instead of acid chlorides 6, 8, and 10, the corresponding acids can be used to prepare intermediates 11, 12, and 13 (using HBTU-mediated coupling).

Compound 3. A mixture of 4-iodoaniline 2 (9.39 g, 42.8 mmol) and $Boc_2O$ (8.78 g, 47.1 mmol) in DMF (25 mL) and DIEA (5 mL) was stirred at RT for 3 hr, diluted with AcOEt (300 mL), and washed with $H_2O$ (2×, each 150 mL). The organic layer was dried ($MgSO_4$) and evaporated to give compound 3 (11.89 g, 87%, $^1$H-NMR).

Compound 4. Coupling of compounds 1 (679 mg, 4.19 mmol) and 3 (1.21 g, 3.79 mmol) according to procedure A gave compound 4 (0.50 g, 43%, white powder, $^1$H-NMR).

Compound 5. A solution of compound 4 (472 mg) in AcOEt (150 mL, saturated with anhydrous HCl gas) was stirred at RT for 4 hr and diluted with $Et_2O$ (100 mL). The resulting precipitate was collected by filtration and dried to give compound 5 (315 mg, >95%, $^1$H-NMR).

Compound 11. A mixture of acid 7 (1.06 g, 5.35 mmol) and HBTU (1.93 g, 5.09 mmol) in NMP (4 mL) and DIEA (1 mL) was stirred at RT for 40 min and added to a solution of compound 5 (0.935 g, 4.47 mmol) in NMP (2 mL) and DIEA (0.5 mL). The mixture was stirred for 1 hr at RT and added dropwise to 10% aqueous $K_2CO_3$ (200 mL) at ca. 4° C. The resulting precipitate was collected by filtration and dried in vacuo to give compound 11 ($^1$H-NMR; used without further purification).

Compound 12. A mixture of acid 9 (1.04 g, 6.62 mmol) and HBTU (2.39 g, 6.30 mmol) in NMP (9 mL) and DIEA (1.5 mL) was stirred at 37° C. for 30 min and added to a solution of compound 5 (1.16 g, 5.55 mmol) in NMP (2 mL) and DIEA (0.5 mL). The mixture was stirred for 17 hr at RT followed by 5 hr at 60° C. and added dropwise to 10% aqueous K$_2$CO$_3$ (400 mL) at ca. 4° C. The resulting precipitate was collected by filtration and dried in vacuo to give compound 12 (1.70 g; $^1$H-NMR spectrum; contained impurities but was used without further purification).

Compound 13. Coupling of acid chloride 10 (0.222 mL, 1.68 mmol) and compound 5 (0.318 g, 1.29 mmol) according to Procedure C gave compound 13 as a tan solid (505 mg, $^1$H-NMR; contained minor impurities but was used without further purification).

Figure 2:
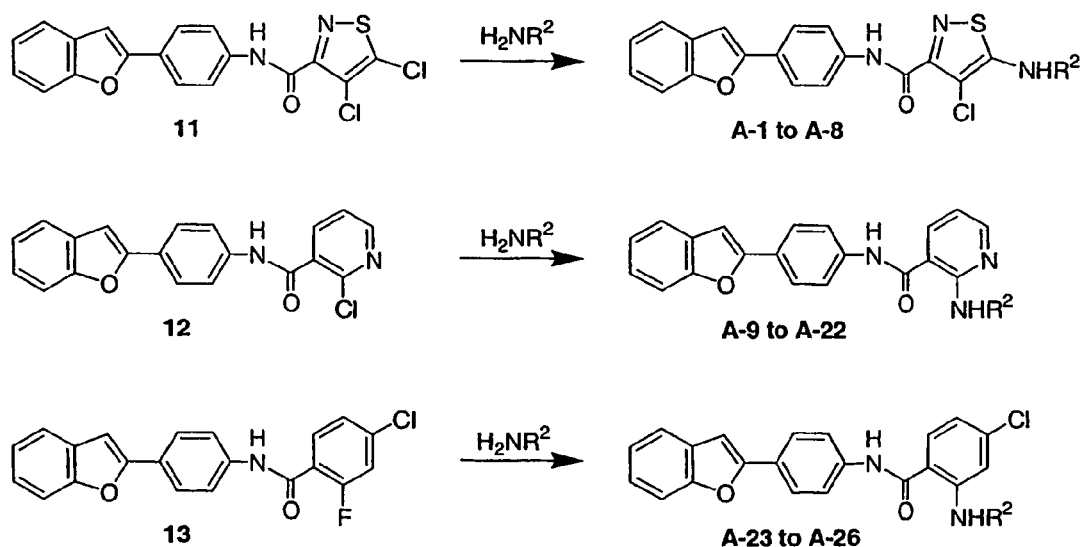

Next, FIG. 2 illustrates the synthesis of compounds A-1 to A-26 from intermediates previously synthesized. The regioselectivity of the nucleophilic aromatic substitution at the isothiazole unit in intermediate 11 was confirmed by the X-ray structure of a model compound, while the structures of compounds A-23 to A-26 were unambiguously assigned by $^1$H-NMR.

Compounds A-1 to A-8. These compounds were prepared from compound 11 (70 mg) in a mixture of the corresponding amine (0.3-1 mL) and NMP (0.1-0.5 mL), 60° C., 24 hours, according to Procedure D.

Compounds A-9 to A-22. Compounds A-11 and A-13 to A-21 were prepared from compound 12 (80 mg) and the corresponding amine (ca. 0.2 mL) in NMP (1 mL) and DIEA (0.2 mL), 60° C., 17-24 hr, according to Procedure D. Compounds A-9, A-10, A-12, and A-22 were prepared analogously.

Compounds A-23 to A-26. These compounds were prepared from compound 13 (50 mg) in a mixture of the corresponding amine (0.4 mL) and NMP (0.4 mL), 75° C., 24 hr, according to Procedure D.

EXAMPLE B

This example describes the synthesis of biaryl compounds wherein the biaryl moiety comprises a benzofuryl unit and a methylated phenyl unit.

Figure 3:
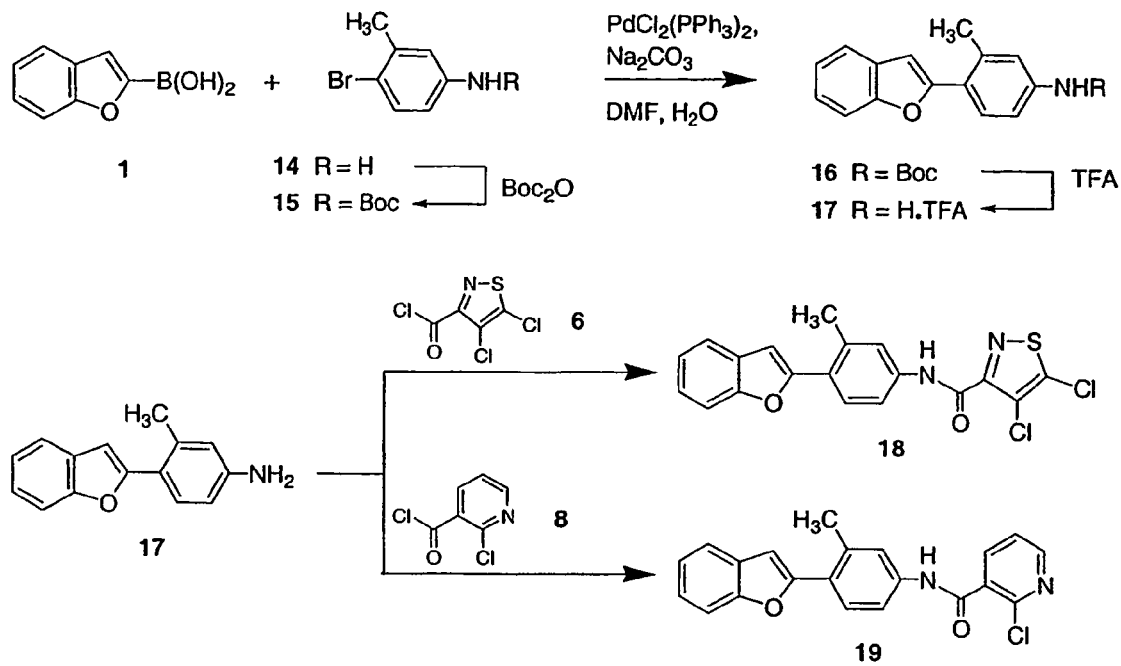

The synthesis of the intermediates 18 and 19 is shown in FIG. 3.

Compound 15. Compound 15 was prepared by Boc-protection of aniline 14 by analogy to the preparation of compound 3.

Compound 16. Coupling of compounds 1 (1.55 g, 9.60 mmol) and 15 (2.50 g, 8.73 mmol) according to Procedure A gave intermediate 16 (2.00 g, 71%, white solid, $^1$H-NMR).

Compound 17. Deprotection of intermediate 16 (2.00 g) according to Procedure B gave compound 17 (>95%, white solid, $^1$H-NMR).

Compound 18. Coupling of compounds 17 (0.70 g, 2.07 mmol) and 6 (0.494 g, 2.28 mmol) according to Procedure C gave compound 18 ($^1$H-NMR).

Compound 19. Coupling of compounds 17 (0.70 g, 2.07 mmol) and 8 (0.40 g, 2.28 mmol) according to Procedure C gave compound 19 ($^1$H-NMR).

Figure 4:
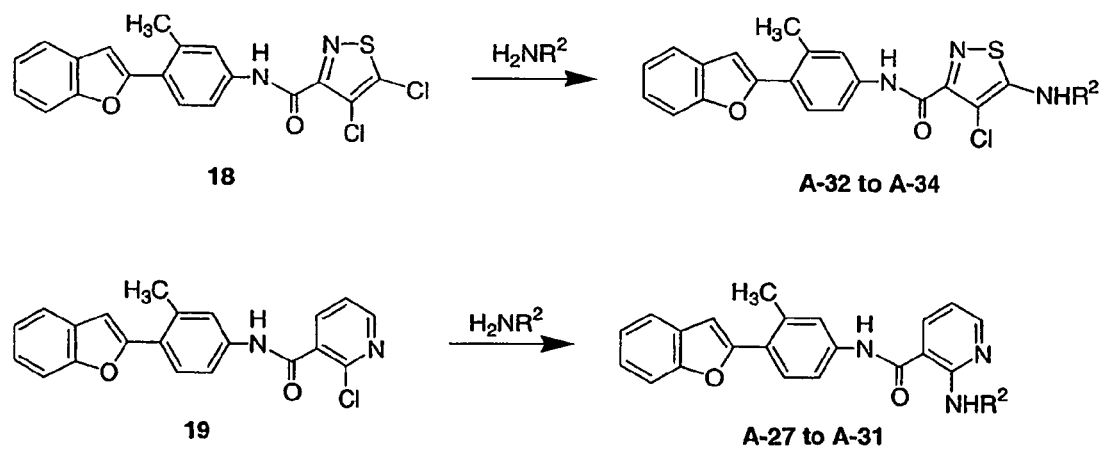

Intermediates 18 and 19 were converted to compounds A-27 to A-34, as shown in FIG. 4.

Compounds A-27 to A-31. These compounds were prepared from compound 19 (80 mg) in a mixture of the corresponding amine H$_2$NR$^2$ (0.4 mL) and NMP (1 mL), 70° C., 72 hr, according to Procedure D.

Compounds A-32 to A-34. These compounds were prepared from compound 18 (80 mg) in a mixture of the corresponding amine H$_2$NR$^2$ (0.4 mL) and NMP (1 mL), 70° C., 72 hr, according to Procedure D.

EXAMPLE C

Figure 5:
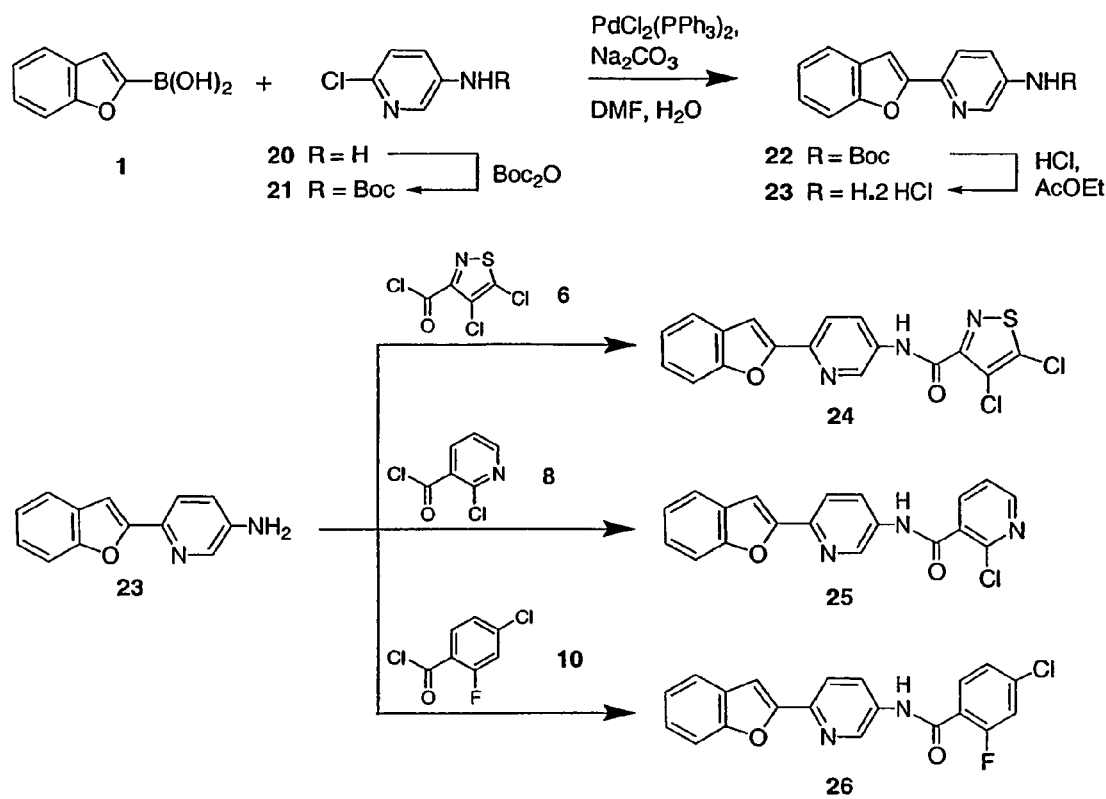

This example describes the synthesis of compounds containing a benzofuryl moiety and various N-termini. The internal heterocyclic unit is a disubstituted pyridine. Intermediates 24 to 26 were prepared by Suzuki-type coupling of benzofuryl boronic acid 1 and chloropyridine 21 as the key step, as shown in FIG. 5.

Compound 21. A mixture of pyridine 20 (5.37 g, 41.9 mmol) and Boc$_2$O (8.56 g, 46.1 mmol) in DMF (25 mL) and DIEA (5 mL) was stirred at RT for 4 hr, then at 60° C. for 16 hr. The solution was diluted with AcOEt (300 mL) and was washed with 10% aqueous K$_2$CO$_3$ (2×, each 100 mL). The organic layer was dried (MgSO$_4$) and evaporated to give compound 21 (8.27 g, 87%, $^1$H-NMR).

Compound 22. Coupling of boronic acid 1 (841 mg, 5.19 mmol) and compound 21 (1.08 g, 4.72 mmol) according to Procedure A gave compound 22 (1.07 g, 73%, white crystals, $^1$H-NMR).

Compound 23. A mixture of compound 22 (0.98 g) in AcOEt (50 mL, saturated with anhydrous HCl gas) was stirred at 0° C. to RT for 9 hr and treated with Et$_2$O (200 mL). The resulting solid was collected by filtration and dried to give compound 23 as yellow crystals (0.759 g, 85%, $^1$H-NMR).

Compound 24. Coupling of acid chloride 6 (1.34 g, 6.17 mmol) and compound 23 (2.00 g, 6.17 mmol) according to Procedure C gave compound 24 ($^1$H-NMR).

Compound 25. Coupling of acid chloride 8 (1.09 g, 6.17 mmol) and compound 23 (2.00 g, 6.17 mmol) according to Procedure C gave compound 25 ($^1$H-NMR; minor impurities but used for the next step without further purification).

Compound 26. Coupling of acid chloride 10 (0.815 mL, 6.17 mmol) and compound 23 (2.00 g, 6.17 mmol) according to Procedure C gave compound 26 ($^1$H-NMR; minor impurities but used for the next step without further purification).

Figure 6:
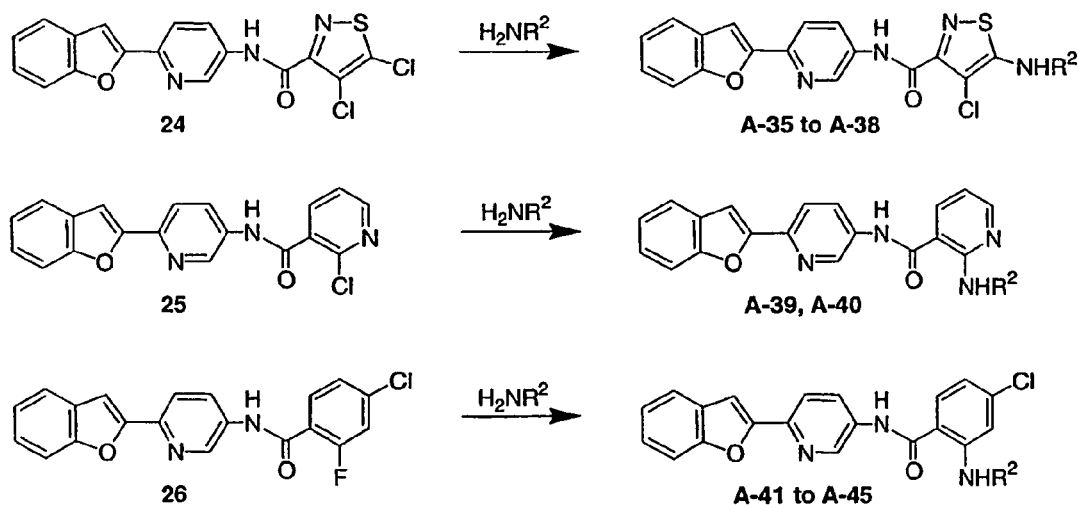

The conversion of intermediates 24, 25, and 26 to compounds A-35 to A45 is shown in FIG. 6.

Compounds A-35 to A-38. These compounds were prepared from compound 24 (80 mg) in a mixture of the corresponding amine H$_2$NR$^2$ (0.4 mL) and NMP (1 mL), 75° C., 48 hr, according to Procedure D.

Compounds A-39 and A-40. These compounds were prepared from compound 25 (100 mg for compound A-39; 80 mg for compound A-40) in a mixture of the corresponding amine H$_2$NR$^2$ (0.5 mL for compound A-39; 0.4 mL for compound A-40) and NMP (0.5 mL for compound A-39; 1 mL for compound A-40), 75° C., 48 hr, according to Procedure D.

Compounds A-41 to A-45. These compounds were prepared from compound 26 (80 mg; except 100 mg for compound A-41) in a mixture of the corresponding amine H$_2$NR$^2$ (0.4 mL; except 0.5 mL for compound A-41) and NMP (1 mL; except 0.5 mL for A41), 75° C., 48 hr, according to Procedure D.

EXAMPLE D

This example describes the synthesis of compounds having a ring nitrogen in the benzofuryl unit, as exemplified by compound A-55.

Figure 7:
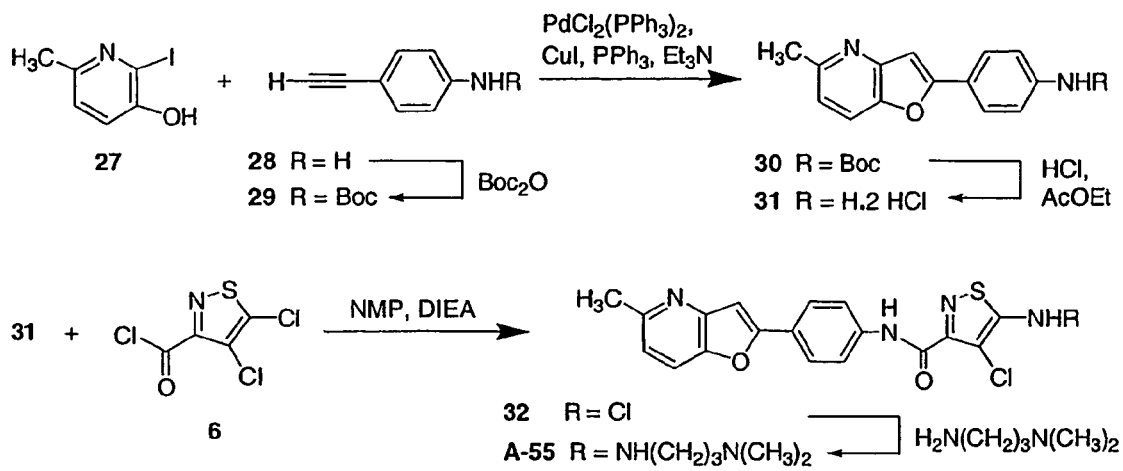

The key step is a Sonogashira-type coupling of arylalkyne 29 to iodopicolinol 27 (FIG. 7). The product of the C—C bond formation spontaneously undergoes a Pd-mediated cyclization to desired product 30. Deprotection of product 30 under acidic conditions gave aniline 31, which was coupled to acid chloride 6 to yield intermediate 32. Nucleophilic aromatic substitution at the isothiazole ring in intermediate 32 gave compound A-55.

Compound 29. Compound 29 was prepared by Boc-protection of compound 28, analogously to the preparation of compound 3.

Compound 30. A degassed ($N_2$) suspension of picolinol 27 (0.50 g, 2.12 mmol), $PdCl_2(PPh_3)_2$ (30 mg, 0.04 mmol), CuI (32 mg, 0.17 mmol), and $PPh_3$ (44 mg, 0.16 mmol) in $Et_3N$ (10 mL) was treated at RT with alkyne 28 (508 mg, 2.34 mmol) and stirred at 70° C. for 2 hr. Evaporation of the solvent and purification of the residual material by flash chromatography (hexane/AcOEt, 19:1 to 3:2 gradient) gave compound 30 (153 mg, 22%, $^1$H-NMR).

Compound 31. Compound 30(100 mg) in AcOEt (4 mL, saturated with anhydrous HCl gas) was stirred at RT for 6 hr and diluted with $Et_2O$ (50 mL). The resulting precipitate was collected by filtration and dried to give compound 31 as a yellow solid (85 mg, 93%, $^1$H-NMR).

Compound A-55. A mixture of acid chloride 6 (17.2 mg, 80 μmol) and amine 31 (20 mg, 67 μmol) in NMP (0.33 mL) and DIEA (0.03 mL) was stirred at 60° C. for 12 hr to give compound 32, which was converted in situ to compound A-55 by treatment with 3-(dimethylamino)propylamine (1 mL), stirring at 70° C. for 24 hr, dilution with 50% aqueous AcOH to a total volume of 15 mL and purification by HPLC ($^1$H-NMR, ESI-MS).

EXAMPLE E

Figure 8:
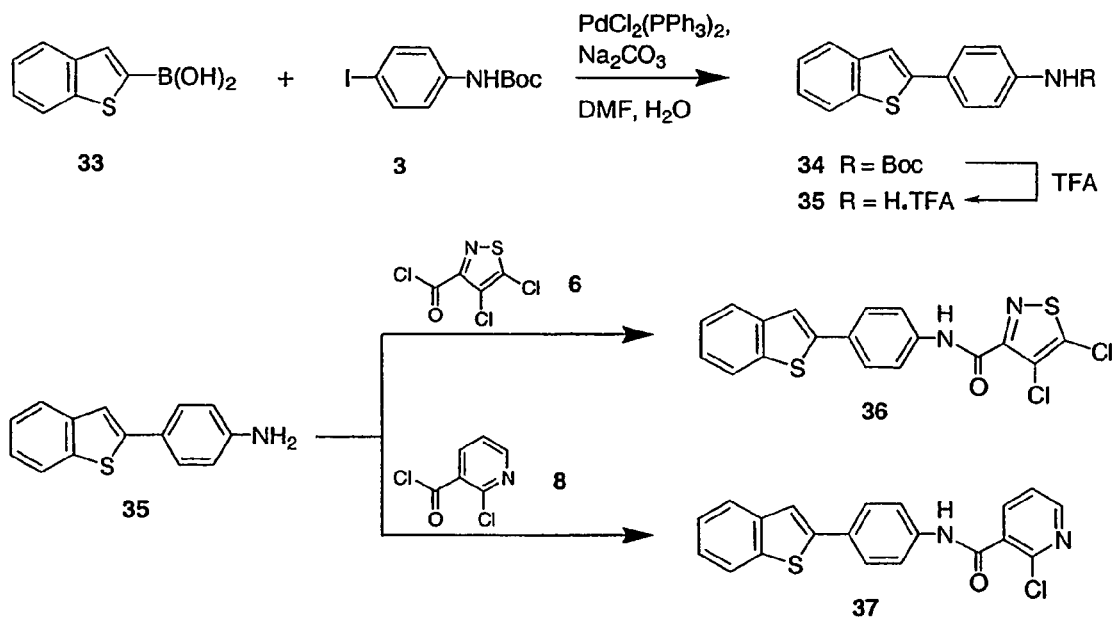

This example describes the synthesis of compounds containing a benzothienyl moiety. As shown in FIG. 8, the benzothienyl-containing biaryl unit was formed under Suzuki-type conditions starting from boronic acid 33 and iodoaniline 3.

Compound 34. Coupling of boronic acid 33 (1.50 g, 8.42 mmol) and protected iodoaniline 3 (2.44 g, 7.66 mmol) according to Procedure A gave biaryl compound 34 (1.56 g, 63%, tan solid, $^1$H-NMR).

Compound 35. Deprotection of biaryl compound 34 (1.56 g) according to Procedure B gave 35 (>95%, $^1$H-NMR; contained residual TFA but used without further purification).

Compound 36. Coupling of acid halide 6 (498 mg, 2.30 mmol) and compound 35 (650 mg, 1.92 mmol) according to Procedure C gave triaryl compound 36 ($^1$H-NMR).

Compound 37. Coupling of acid halide 8 (405 mg, 2.30 mmol) and compound 35 (650 mg, 1.92 mmol) according to Procedure C gave triaryl compound 37 ($^1$H-NMR).

Figure 9:
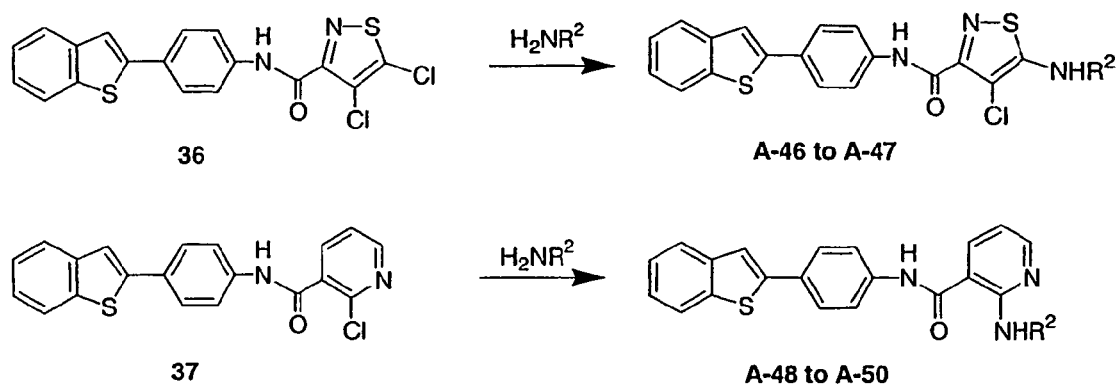

The preparation of compounds A-46 to A-50 from triaryl intermediates 36 and 37 is illustrated in FIG. 9.

Compounds A-46 and A-47. These compounds were prepared from compound 36 (80 mg) in a mixture of the corresponding amine $H_2NR^2$ (0.4 mL) and NMP (1 mL), 75° C., 48 hr, according to Procedure D.

Compounds A-48 to A-50. These compounds were prepared from compound 37 (80 mg) in a mixture of the corresponding amine $H_2NR^2$ (0.4 mL) and NMP (1 mL), 75° C., 48 hr, according to Procedure D.

EXAMPLE F

Figure 10:
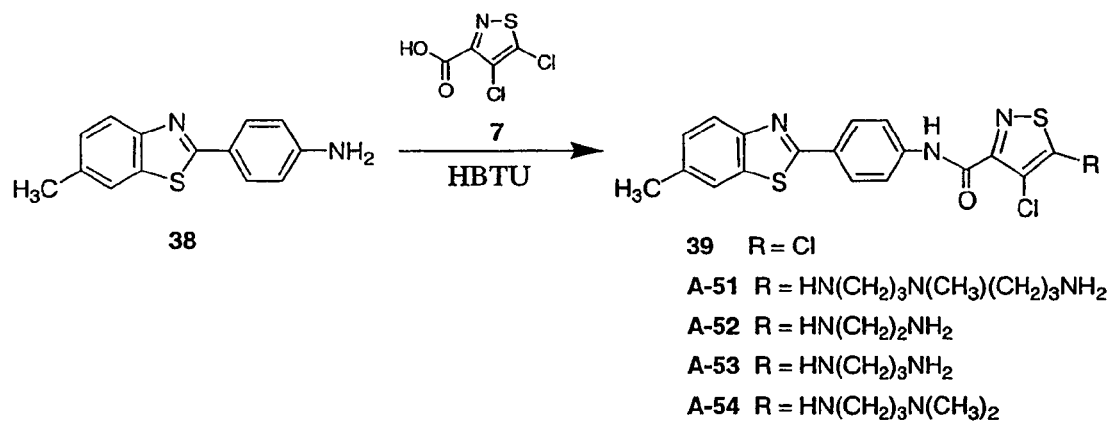

This example describes the synthesis of compounds containing a benzothiazole moiety from the commercially available compound 38 (FIG. 10).

Compound 39. A mixture of acid 7 (1.812 g, 9.20 mmol) and HBTU (3.314 g, 8.74 mmol) in DMF (10 mL) and DIEA (3 mL) was stirred at RT for 1 hr. The mixture was added to a solution of compound 38 (2.0 g, 8.32 mmol) in DMF (16 mL) and DIEA (2 mL). The reaction mixture was stirred at 60° C. for 24 hr and poured into stirred ice-water (ca. 700 mL). The resulting precipitate was collected by filtration and dried to give compound 39 as a tan solid (2.33 g) ($^1$H-NMR; minor impurities but used without further purification).

Compounds A-51 to A-54. These compounds were prepared according to Procedure D using compound 39 (100 mg), the corresponding amine $H_2NR^2$ (0.4 mL), NMP (1 mL), and DIEA (0.1 mL).

EXAMPLE G

This example describes the synthesis of compounds in which the biaryl unit contains an indole moiety.

Figure 11:
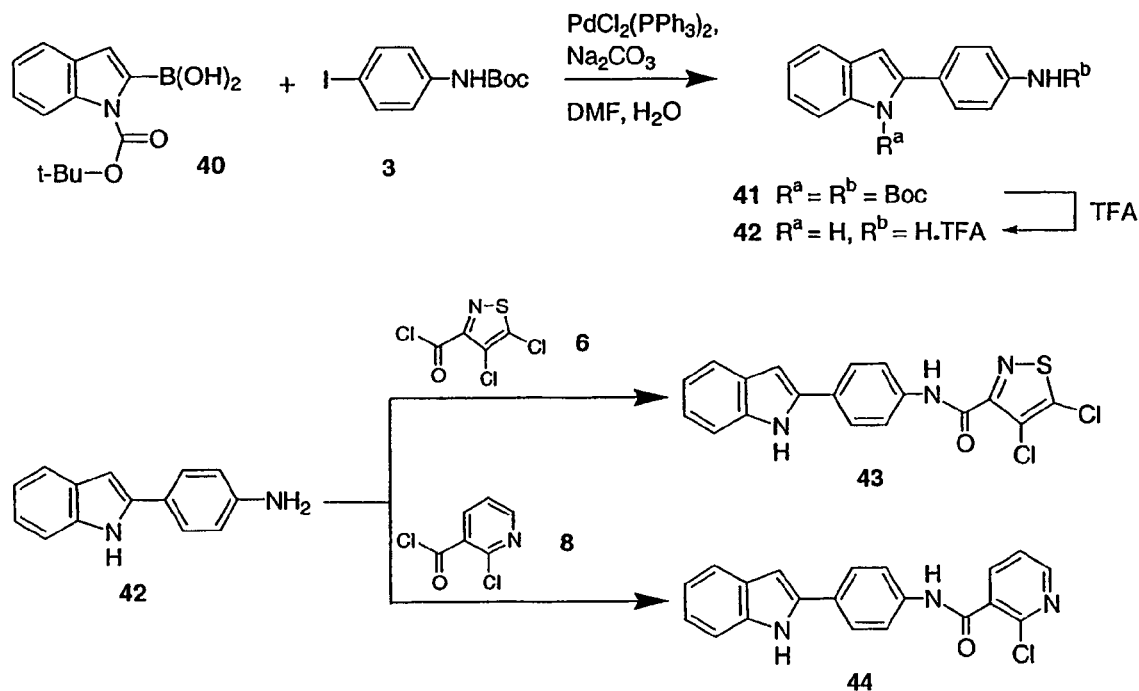

FIG. 11 shows the synthesis of intermediates 43 and 44.

Compound 41. Coupling of protected boronic acid 40 (1.00 g, 3.83 mmol) and protected iodoaniline 3 (1.11 g, 3.48 mmol) according to Procedure A gave compound 41 (1.19 g, 83%, tan solid, $^1$H-NMR).

Compound 42. Deprotection of compound 41 (1.19 g) according to Procedure B gave compound 42 (923 mg; >95%; $^1$H-NMR; contained residual TFA but used without further purification).

Compound 43. Coupling of acid halide 6 (378 mg, 1.75 mmol) and compound 42 (450 mg, 1.40 mmol) according to Procedure C gave intermediate 43 ($^1$H-NMR).

Compound 44. Coupling of acid halide 8 (321 mg, 1.82 mmol) and compound 42 (470 mg, 1.46 mmol) according to Procedure C gave compound 44 ($^1$H-NMR; minor impurities but used without further purification).

Figure 12:
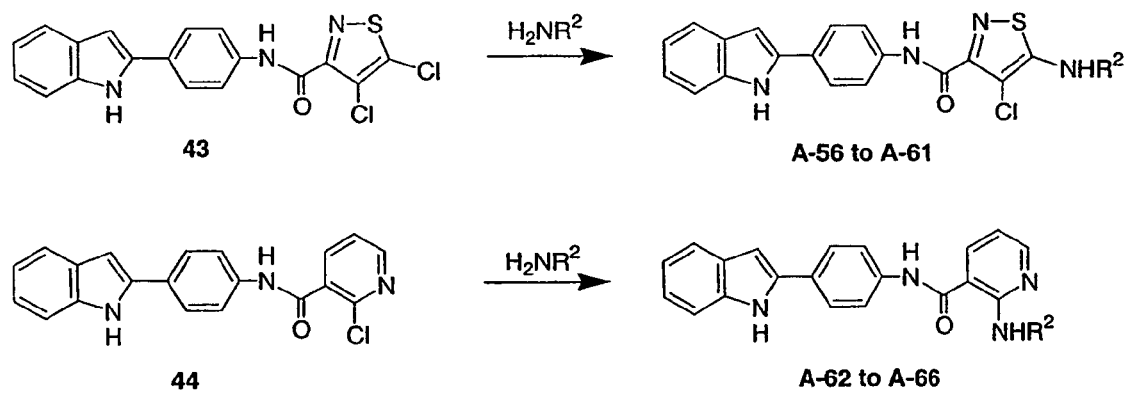

FIG. 12 shows the conversion of compounds 43 and 44 to compounds of this invention.

Compounds A-56 and A-61. These compounds were prepared from compound 43 (70 mg) in a mixture of the corresponding amine $H_2NR^2$ (0.4 mL) and NMP (1 mL), 75° C., 48 hr, according to Procedure D.

Compounds A-62 and A-66. These compounds were prepared from compound 44 (80 mg) in a mixture of the corresponding amine $H_2NR^2$ (0.4 mL) and NMP (1 mL), 75° C., 48 hr, according to Procedure D.

EXAMPLE H

This example describes the synthesis of compounds in which the biaryl moiety is a benzothienyl-pyridyl moiety.

Figure 13:
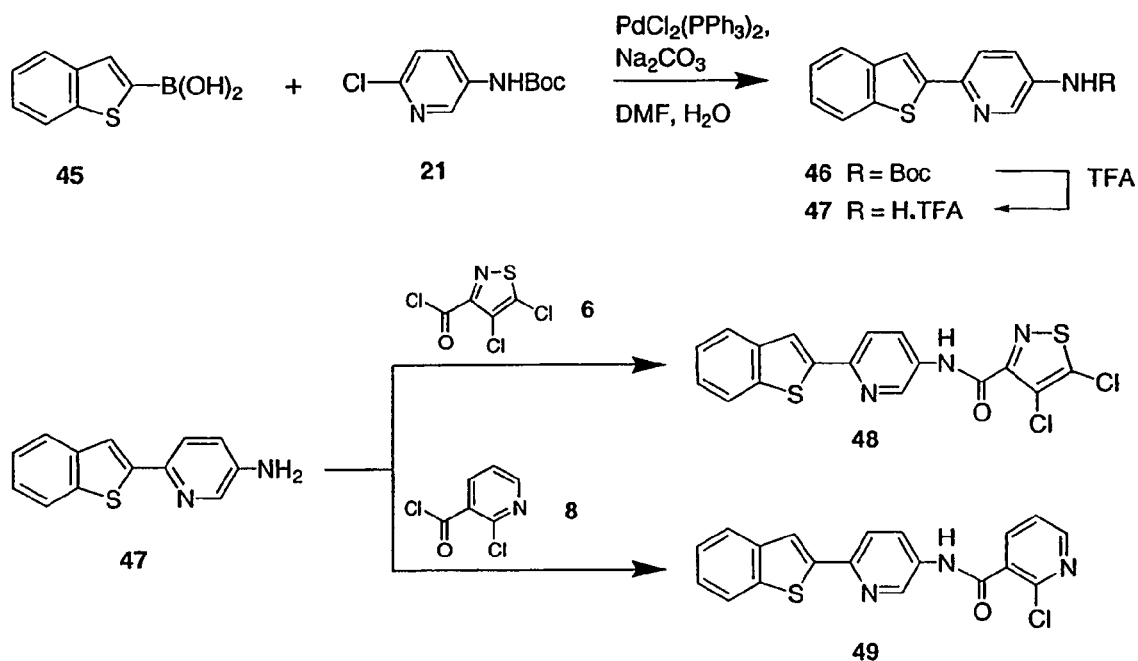

FIG. 13 shows the synthesis of intermediates 48 and 49.

Compound 46. Coupling of boronic acid 45 (2.00 g, 11.2 mmol) and chloropyridine 21 (2.34 g, 10.2 mmol) according to Procedure A gave biaryl compound 46 (1.94 g, 58%, white solid, $^1$H-NMR).

Compound 47. Deprotection of biaryl compound 46 (2.40 g) according to Procedure B gave compound 47 (2.40 g, orange solid, $^1$H-NMR, contained residual TFA but used without further purification).

Compound 48. Coupling of acid chloride 6 (525 mg, 2.42 mmol) and compound 47 (750 mg, 2.20 mmol) according to Procedure C gave intermediate 48 (used without characterization).

Compound 49. Coupling of acid chloride 8 (427 mg, 2.42 mmol) and compound 47 (750 mg, 2.20 mmol) according to Procedure C gave intermediate 49 (used without characterization).

Figure 14:
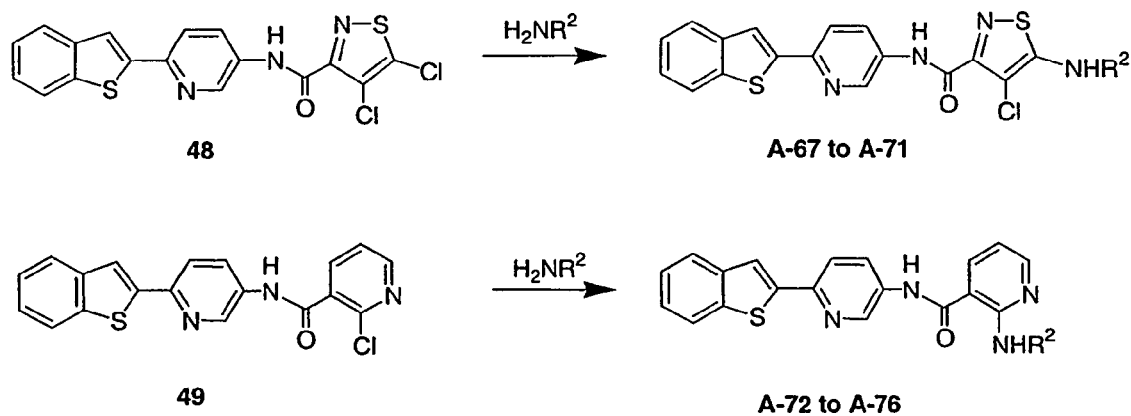

FIG. 14 shows the conversion of intermediates 48 and 49 to compounds of this invention.

Compounds A-67 to A-71. These compounds were prepared from intermediate 48 (100 mg) in a mixture of the corresponding amine $H_2NR^2$ (0.5 mL) and NMP (0.5 mL), 75° C., 48 hr, according to Procedure D.

Compounds A-72 to A-76. These compounds were prepared from intermediate 49 (100 mg) in a mixture of the corresponding amine $H_2NR^2$ (0.5 mL) and NMP (0.5 mL), 75° C., 48 hr, according to Procedure D.

Biological Activity

In vitro biological activity data were collected for a variety of microorganisms, including *Bacillus cereus* (ATCC 11778), *Staphylococcus aureus* (ATCC 33591; ATCC 27660, a methicillin resistant strain (MRSA); ATCC 13709, a methicillin sensitive strain (MSSA)), *Escherichia coli* (ATCC 25922), *Enterococcus faecalis* (ATCC 29212), *Streptococcus pneumoniae* (ATCC 49619; ATCC 51422, a penicillin resistant strain (PRSP)), *Enterococcus faecium* (ATCC 51559, a vancomycin resistant strain (VRE)), and *Staphylococcus epidermidis* (ATCC 12228). Additionally, antifungal activity data were collected for *Candida albicans* (ATCC 38247). Compounds of this invention preferably have an MIC of 4 or less against a drug resistant bacterial strain, such as one of the foregoing (MRSA, VRE, PRSP)

Compounds according to this invention were screened for their in vitro activities against selected species of bacteria and fungi. The minimal inhibition concentration (MIC) of these compounds was determined using the National Committee for Clinical Laboratory Standards (NCCLS) broth microdilution assay in microtiter plates, as set forth in: (1) the guidelines of the National Committee for Clinical Laboratory Standards (NCCLS) Document M7-A4 (NCCLS, 1997); (2) the guidelines of the National Committee for Clinical Laboratory Standards (NCCLS) Document M11-A4 (NCCLS, 1997); and (3) the guidelines and reference method of the National Committee for Clinical Laboratory Standards (NCCLS) Document M27 -T (NCCLS, 1995). For antifungal assays, the method recommended in Murray, PR., 1995 *Manual of Clinical Microbiology* (ASM Press, Washington, D.C.), was employed.

Preferably, compounds of this invention have an MIC of 4 or less against at least one strain of drug resistant bacteria. The results are presented in Table B below, which is keyed as follows:

TABLE B

Biological Activity

Organism (Minimum Inhibitory Concentration (MIC), µg/mL)

| Ref. | A | B | C | D | E | F | G | H | I |
|---|---|---|---|---|---|---|---|---|---|
| A-1 | +++ | + | +++ | +++ | +++ | ND | ND | + | >32 |
| A-2 | +++ | ++ | +++ | +++ | +++ | +++ | +++ | + | >32 |
| A-3 | + | +++ | +++ | +++ | +++ | +++ | +++ | + | >32 |
| A-4 | + | + | +++ | +++ | +++ | ND | ND | >32 | >32 |
| A-5 | ++ | ++ | +++ | +++ | +++ | ND | ND | >32 | >32 |
| A-6 | >32 | ++ | +++ | +++ | +++ | ND | ND | >32 | >32 |
| A-7 | +++ | ++ | +++ | +++ | +++ | +++ | +++ | + | >32 |
| A-8 | +++ | ++ | +++ | +++ | +++ | +++ | +++ | + | + |
| A-9 | +++ | + | +++ | +++ | +++ | ND | ND | + | + |
| A-10 | + | >32 | + | ND | ND | ND | ND | + | >32 |
| A-11 | +++ | +++ | +++ | +++ | +++ | +++ | +++ | + | >32 |
| A-12 | + | + | ++ | ND | ND | ND | + | ++ | >32 |
| A-13 | +++ | + | +++ | +++ | +++ | ND | ND | + | >32 |
| A-14 | >32 | >32 | >32 | >32 | >32 | ND | ND | >32 | >32 |
| A-15 | ++ | + | +++ | +++ | +++ | ND | ND | + | >32 |
| A-16 | >32 | + | ++ | +++ | +++ | ND | ND | + | >32 |
| A-17 | + | + | + | ++ | + | ND | ND | + | >32 |
| A-18 | +++ | ++ | ++ | +++ | +++ | +++ | +++ | +++ | >32 |
| A-19 | +++ | ++ | +++ | +++ | +++ | +++ | +++ | + | >32 |
| A-20 | + | ++ | + | ++ | ++ | ND | ND | + | + |
| A-21 | ++ | +++ | +++ | +++ | +++ | ND | ND | + | >32 |
| A-22 | ++ | +++ | ++ | ++ | ++ | ND | ND | + | >32 |
| A-23 | +++ | + | +++ | +++ | +++ | +++ | ND | + | >32 |
| A-24 | >32 | >32 | + | + | + | + | ND | >32 | >32 |
| A-25 | >32 | >32 | + | + | + | + | ND | >32 | >32 |
| A-26 | + | >32 | ++ | +++ | ++ | ++ | ND | + | >32 |
| A-27 | ++ | ++ | +++ | +++ | +++ | +++ | ND | + | >32 |
| A-28 | + | + | ++ | ++ | ++ | ++ | ND | + | >32 |
| A-29 | +++ | + | +++ | +++ | +++ | +++ | ND | + | >32 |
| A-30 | ++ | + | +++ | +++ | +++ | +++ | ND | + | >32 |
| A-31 | ++ | ++ | +++ | +++ | +++ | +++ | ND | + | ++ |
| A-32 | >32 | ++ | +++ | +++ | +++ | +++ | +++ | ND | + |
| A-33 | >32 | + | ++ | +++ | +++ | + | ND | + | >32 |
| A-34 | +++ | +++ | +++ | +++ | +++ | +++ | +++ | + | >32 |
| A-35 | >32 | +++ | + | + | + | >32 | ND | >32 | >32 |
| A-36 | ++ | ++ | ++ | +++ | + | ++ | ND | + | >32 |
| A-37 | >32 | + | ++ | +++ | +++ | ++ | ND | >32 | >32 |
| A-38 | +++ | + | +++ | +++ | +++ | +++ | ND | >32 | >32 |
| A-39 | + | >32 | + | + | + | + | ND | + | >32 |
| A-40 | + | + | ++ | ++ | ++ | + | ND | >32 | + |
| A-41 | ++ | ++ | +++ | +++ | +++ | +++ | ND | + | ++ |
| A-42 | ++ | >32 | ++ | ++ | ++ | ND | ++ | + | >32 |
| A-43 | ++ | >32 | ++ | ++ | ++ | ++ | ND | + | >32 |
| A-44 | ++ | ++ | ++ | ++ | ++ | ++ | ND | + | >32 |
| A-45 | ++ | ++ | ++ | +++ | +++ | +++ | ND | + | >32 |
| A-46 | >32 | >32 | >32 | + | + | >32 | ND | >32 | >32 |
| A-47 | >32 | +++ | +++ | +++ | +++ | +++ | +++ | >32 | >32 |
| A-48 | + | >32 | >32 | +++ | +++ | +++ | ND | >32 | >32 |
| A-49 | +++ | +++ | +++ | +++ | +++ | +++ | +++ | + | >32 |
| A-50 | +++ | +++ | +++ | +++ | +++ | +++ | +++ | + | >32 |
| A-51 | +++ | +++ | +++ | +++ | +++ | ND | ND | +++ | >32 |
| A-52 | + | >32 | +++ | +++ | ND | +++ | ND | >32 | >32 |
| A-53 | +++ | >32 | +++ | +++ | +++ | +++ | +++ | >32 | >32 |
| A-54 | +++ | +++ | +++ | +++ | +++ | +++ | ND | + | >32 |
| A-55 | + | ++ | + | ++ | ++ | + | ND | + | >32 |
| A-56 | >32 | + | + | ++ | ++ | ++ | ND | >32 | >32 |
| A-57 | + | +++ | ++ | ++ | ++ | + | ND | >32 | >32 |
| A-58 | + | +++ | ++ | + | ++ | ++ | ND | + | >32 |
| A-59 | + | +++ | +++ | ++ | ++ | + | ND | + | >32 |
| A-60 | >32 | >32 | >32 | >32 | >32 | >32 | ND | >32 | >32 |
| A-61 | >32 | +++ | >32 | >32 | >32 | >32 | ND | >32 | >32 |
| A-62 | >32 | >32 | >32 | >32 | >32 | >32 | ND | >32 | >32 |
| A-63 | + | ++ | ++ | ++ | ++ | ++ | ND | + | >32 |
| A-64 | + | + | + | + | + | + | ND | >32 | + |
| A-65 | + | + | + | + | + | + | ND | >32 | >32 |
| A-66 | >32 | >32 | >32 | >32 | >32 | >32 | ND | >32 | >32 |
| A-67 | +++ | +++ | +++ | +++ | +++ | +++ | ND | >32 | >32 |
| A-68 | +++ | +++ | +++ | +++ | +++ | +++ | +++ | >32 | >32 |
| A-69 | >32 | >32 | >32 | >32 | >32 | >32 | ND | >32 | >32 |
| A-70 | >32 | +++ | +++ | +++ | +++ | +++ | ND | >32 | >32 |
| A-71 | +++ | ++ | +++ | +++ | +++ | +++ | ND | + | +++ |
| A-72 | >32 | >32 | >32 | >32 | >32 | >32 | ND | >32 | >32 |
| A-73 | >32 | >32 | >32 | >32 | >32 | >32 | ND | >32 | >32 |
| A-74 | + | + | ++ | ++ | + | ++ | ND | + | >32 |
| A-75 | +++ | >32 | +++ | +++ | +++ | +++ | ND | + | >32 |
| A-76 | + | + | ++ | +++ | +++ | ++ | ND | + | + |

Key to organisms tested against:
A = *B. cereus* ATCC 11778
B = *C. albicans* ATCC 38247
C = *E. faecalis* ATCC 29212
D = *S. aureus* ATCC 13709
E = *S. aureus* ATCC 27660
F = *S. aureus* ATCC 33591
G = *S. epidermidis* ATCC 12228
H = *S. pneumoniae* ATCC 49619
I = *E. coli* ATCC 25922
Key to activity:
+++ = MIC ≦ 4
++ = 4 < MIC < 12
+ = 12 ≦ MIC ≦ 32
ND = not determined
>32 = preliminary data indicates MIC greater than 32

Table C shows additional antibacterial data for selected compounds, against two drug resistant bacterial strains: *E. faecium* (ATCC 51559, VRE) and *S. pneumoniae* (ATCC 51422, PRSP). (MIC values are keyed in the same manner as Table B.)

TABLE C

Additional Antibacterial Data

| Compound Reference | Organism (Minimum Inhibitory Concentration (MIC), μg/mL) | |
|---|---|---|
| | *E. faecium* (ATCC 51559) | *S. pneumoniae* (ATCC 51422) |
| A-2 | +++ | + |
| A-3 | +++ | + |
| A-7 | +++ | + |
| A-11 | +++ | + |
| A-34 | +++ | + |
| A-53 | +++ | + |
| A-68 | +++ | >32 |

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

What is claimed is:

1. A compound according to the formula

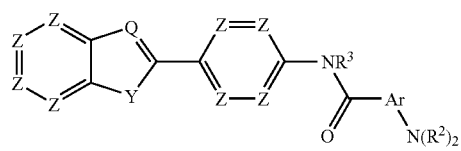

and the pharmaceutically acceptable salts thereof, wherein the moiety:

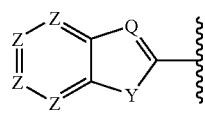

is selected from the group consisting of

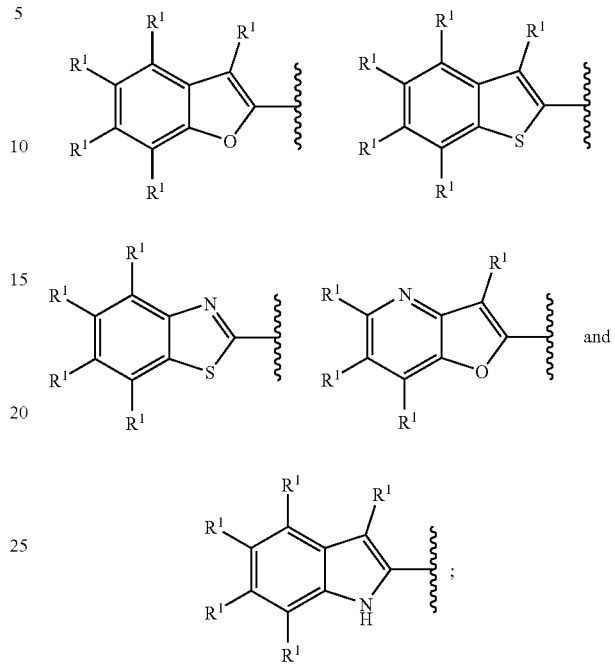

wherein the moiety:

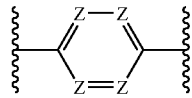

is selected from the group consisting of

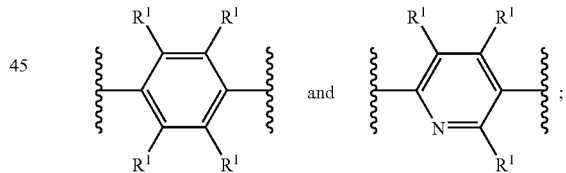

each $R^1$ is independently H, halogen, OH, or a $C_1$ to $C_{12}$ alkyl or heteroalkyl moiety;

each $R^2$ is independently H or a $C_1$ to $C_{18}$ alkyl or heteroalkyl moiety or the two $R^2$'s taken together with the nitrogen atom to which they are attached form a substituted or unsubstituted heteroalkyl 5 to 7 member ring;

wherein the moiety:

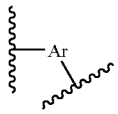

is selected from the group consisting of

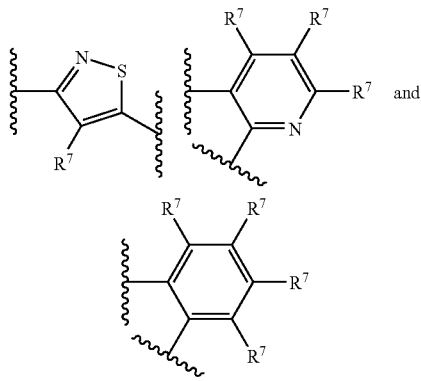

wherein one of $X^1$, $X^2$, and $X^3$ is a ring vertex selected from the group consisting of —O—, —S—, and —$NR^8$—, and the other two of $X^1$, $X^2$, and $X^3$ are ring vertices selected from the group consisting of =N— and =$CR^7$—;

each $R^7$ is independently H, F, Cl, Br, I, CN, OH, $NO_2$, $NH_2$, a substituted or unsubstituted ($C_1$-$C_{12}$)alkyl group, a substituted or unsubstituted ($C_1$-$C_{12}$)alkoxy group, or a substituted or unsubstituted ($C_1$-$C_{12}$)heteroalkyl group;

$R^8$ is H, a substituted or unsubstituted ($C_1$-$C_{12}$)alkyl group, or a substituted or unsubstituted ($C_1$-$C_{12}$)heteroalkyl group; and $R^3$ is H or a $C_1$ to $C_6$ alkyl moiety;

with the proviso that at least one group $R^1$, $R^2$, or $R^3$ contains an alkyl amine group or a quaternary nitrogen group.

2. A compound according to claim 1, wherein at least one group $R^2$ contains an alkyl amine group.

3. A compound according to claim 1 or 2, wherein

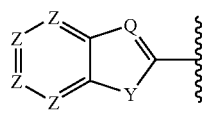

is selected from the group consisting of

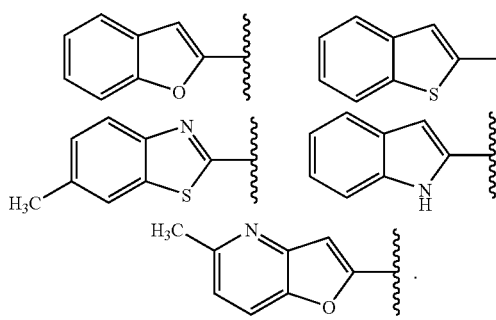

4. A compound according to claim 1 or 2, wherein

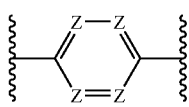

is selected from the group consisting of

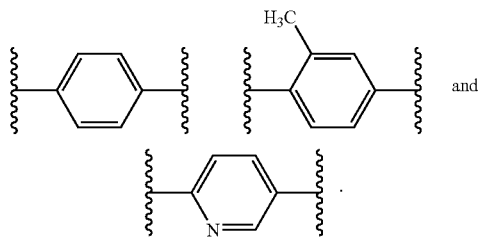

5. A compound according to claim 1 or 2, wherein

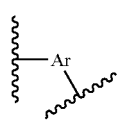

is selected from the group consisting of

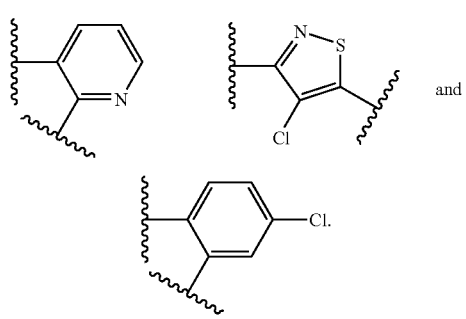

6. A compound according to claim 1 or 2, wherein $R^3$ is H.

7. A compound according to a formula selected from the group consisting of

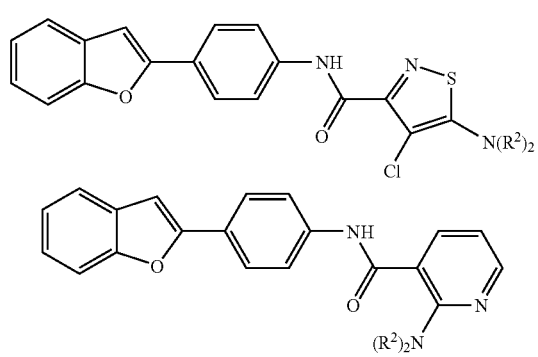

-continued

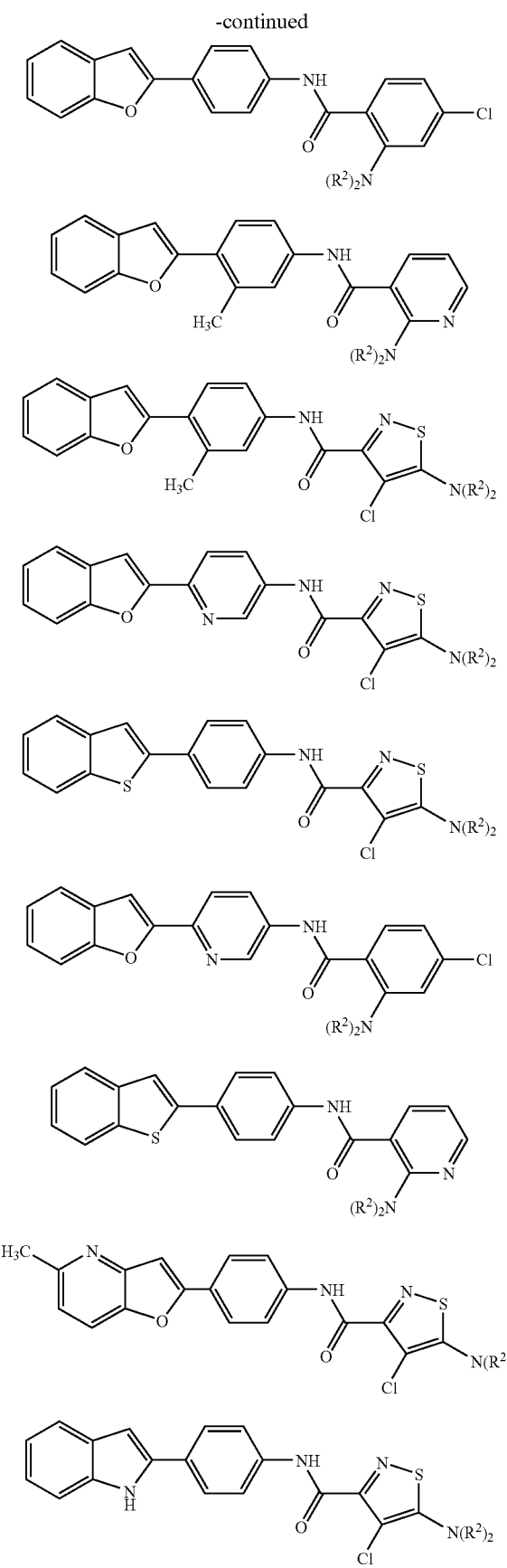

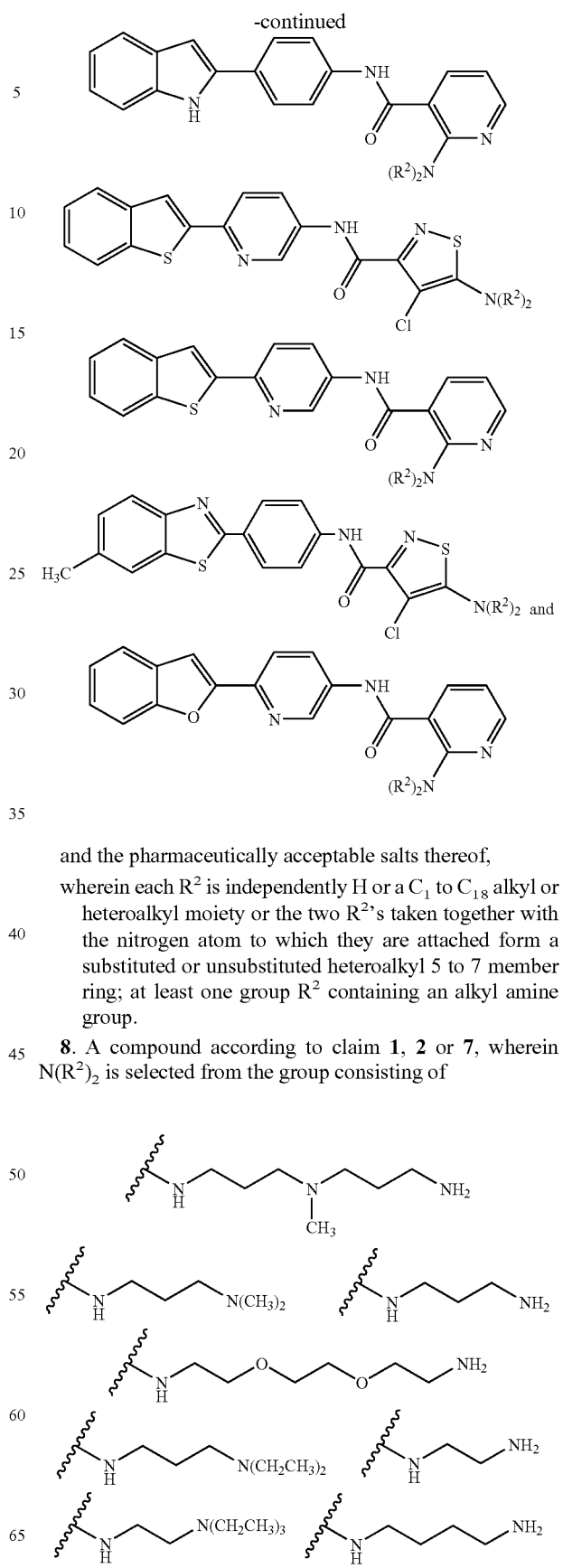

and the pharmaceutically acceptable salts thereof,
wherein each $R^2$ is independently H or a $C_1$ to $C_{18}$ alkyl or heteroalkyl moiety or the two $R^2$'s taken together with the nitrogen atom to which they are attached form a substituted or unsubstituted heteroalkyl 5 to 7 member ring; at least one group $R^2$ containing an alkyl amine group.

8. A compound according to claim 1, 2 or 7, wherein $N(R^2)_2$ is selected from the group consisting of

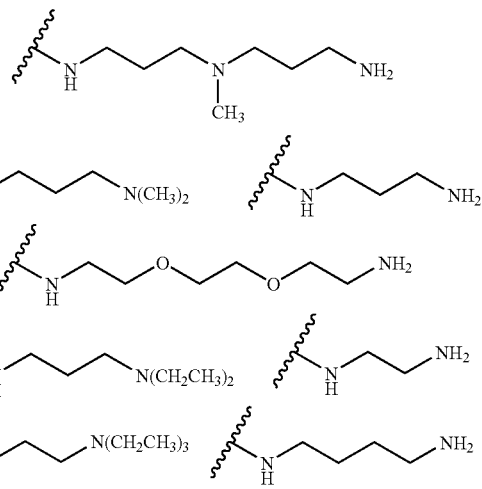

-continued

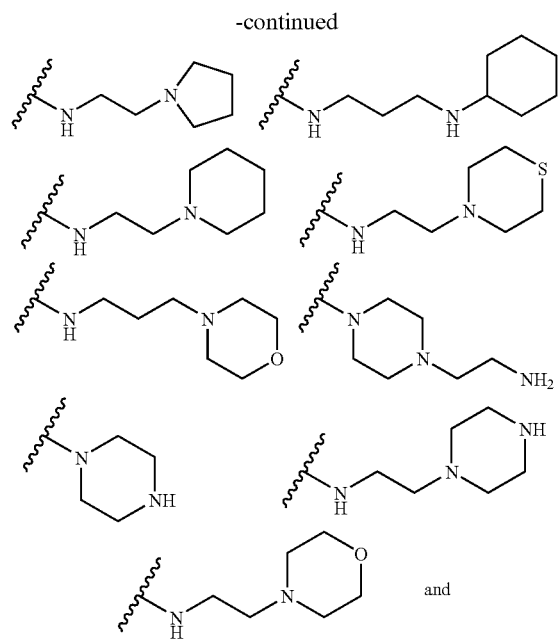

-continued

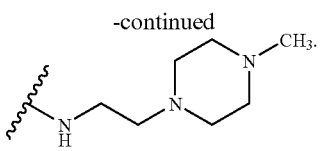

9. A compound according to claim 1, having a minimum inhibitory concentration of 4 μg/mL or less against at least one of *Staphylococcus aureus* (ATCC 27660), *Streptococcus pneumoniae* (ATCC 51422), and *Enterococcus faecium* (ATCC 51559).

10. A method of treating a Gram-positive bacterial infection in a mammal, comprising administering to a patient in need of such treatment an effective amount of a compound according to claim 1, 2, or 7.

11. A method according to claim 10, wherein the bacterial infection is an infection by drug resistant bacteria.

12. A method according to claim 11, wherein the drug resistant bacteria is MRSA, PRSP, or VRE.

13. A compound according to claim 1, wherein $R^1$ is H or $CH_3$.

* * * * *